US011518997B2

(12) United States Patent
D'Halluin

(10) Patent No.: US 11,518,997 B2

(45) Date of Patent: Dec. 6, 2022

(54) TARGETED GENOME ENGINEERING IN PLANTS

(71) Applicant: BASF Agricultural Solutions Seed US LLC, Research Triangle Park, NC (US)

(72) Inventor: Katelijn D'Halluin, Mariakerke (BE)

(73) Assignee: BASF AGRICULTURAL SOLUTIONS SEED US LLC, Research Triangle Park, NC (US)

( * ) Notice: Subject to any disclaimer, the term of this patent is extended or adjusted under 35 U.S.C. 154(b) by 379 days.

(21) Appl. No.: 14/394,277

(22) PCT Filed: Apr. 22, 2013

(86) PCT No.: PCT/EP2013/058264

§ 371 (c)(1),
(2) Date: Oct. 14, 2014

(87) PCT Pub. No.: WO2013/160230

PCT Pub. Date: Oct. 31, 2013

(65) Prior Publication Data

US 2015/0184171 A1 Jul. 2, 2015

Related U.S. Application Data

(60) Provisional application No. 61/636,882, filed on Apr. 23, 2012.

(30) Foreign Application Priority Data

Apr. 23, 2012 (EP) .................................... 12165201

(51) Int. Cl.
*C12N 15/82* (2006.01)
*C12N 9/22* (2006.01)

(52) U.S. Cl.
CPC ..... *C12N 15/8205* (2013.01); *C12N 15/8213* (2013.01); *C12N 9/22* (2013.01); *C12N 15/8243* (2013.01); *C12N 15/8245* (2013.01); *C12N 15/8247* (2013.01); *C12N 15/8255* (2013.01); *C12N 15/8271* (2013.01); *C12N 15/8274* (2013.01); *C12N 15/8279* (2013.01); *C12N 15/8286* (2013.01)

(58) Field of Classification Search
CPC ........................ C12N 15/8205; C12N 15/8213
See application file for complete search history.

(56) References Cited

U.S. PATENT DOCUMENTS 4,693,976 A 9/1987 Schilperoort et al.
4,761,373 A 8/1988 Anderson et al.
4,762,785 A 8/1988 Comai
4,940,838 A 7/1990 Schilperoort et al.
5,004,863 A 4/1991 Umbeck
5,013,659 A 5/1991 Bedbrook et al.
5,104,310 A 4/1992 Saltin
5,141,870 A 8/1992 Bedbrook et al.
5,159,135 A 10/1992 Umbeck
5,177,010 A 1/1993 Goldman et al.
5,231,019 A 7/1993 Paszkowski et al.
5,273,894 A 12/1993 Strauch et al.
5,276,268 A 1/1994 Strauch et al.
5,304,732 A 4/1994 Anderson et al.
5,331,107 A 7/1994 Anderson et al.
5,378,824 A 1/1995 Bedbrook et al.
5,463,174 A 10/1995 Moloney et al.
5,463,175 A 10/1995 Barry et al.
5,464,763 A 11/1995 Schilperoort et al.
5,469,976 A 11/1995 Burchell
5,561,236 A 10/1996 Leemans et al.
5,563,055 A 10/1996 Townsend et al.
5,637,489 A 6/1997 Strauch et al.
5,646,024 A 7/1997 Leemans et al.
5,648,477 A 7/1997 Leemans et al.
5,731,179 A 3/1998 Komari et al.
5,731,180 A 3/1998 Dietrich
5,739,082 A 4/1998 Donn
5,767,361 A 6/1998 Dietrich
5,776,760 A 7/1998 Barry et al.
5,824,790 A 10/1998 Keeling et al.
5,908,810 A 6/1999 Donn
5,928,937 A 7/1999 Kakefuda et al.
6,013,861 A 1/2000 Bird et al.
6,483,013 B1 11/2002 Reynaerts et al.
6,734,341 B2 5/2004 Singletary et al.
6,768,044 B1 7/2004 Boudec et al.

(Continued)

FOREIGN PATENT DOCUMENTS

EP 0267159 A2 5/1988
EP 0159418 B1 5/1990

(Continued)

OTHER PUBLICATIONS

Tohidfa et al (Agrobacterium-mediated transformation of cotton (*Gossypium hirsutum*) using a synthetic cry1Ab gene for enhanced resistance against Heliothis armigera. Iranian Journal of Biotechnology, vol. 6, No. 3 164-173, Jul. 2008).*
Lin et al (Efficient linking and transfer of multiple genes by a multigene assembly and transformation vector system. PNAS. 100, 6962-5967, 2003).*
Kumar et al (Stable transformation of the cotton plastid genome and maternal inheritance of transgenes. Plant Molecular Biology 56: 203-216, 2004).*
Komari et al (Vectors carrying two separate T-DNAs for cotransformation of higher plants mediated by Agrobacterium tumefaciens and segregation of transformants free from selection markers. The Plant Journal. 10(1), 165-174, 1996).*
Breitler et al (A novel two T-DNA binary vector allows efficient generation of marker-free transgenic plants in three elite cultivars of rice (*Oryza sativa* L.). Transgenic Research 13: 271-287, 2004).*

(Continued)

*Primary Examiner* — Charles Logsdon
*Assistant Examiner* — Wayne Zhong
(74) *Attorney, Agent, or Firm* — ArentFox Schiff LLP

(57) ABSTRACT

Improved methods and means are provided to modify in a targeted manner the genome of a plant cell or plant at a predefined site via bacterial transformation.

13 Claims, 4 Drawing Sheets

Figure 1A:
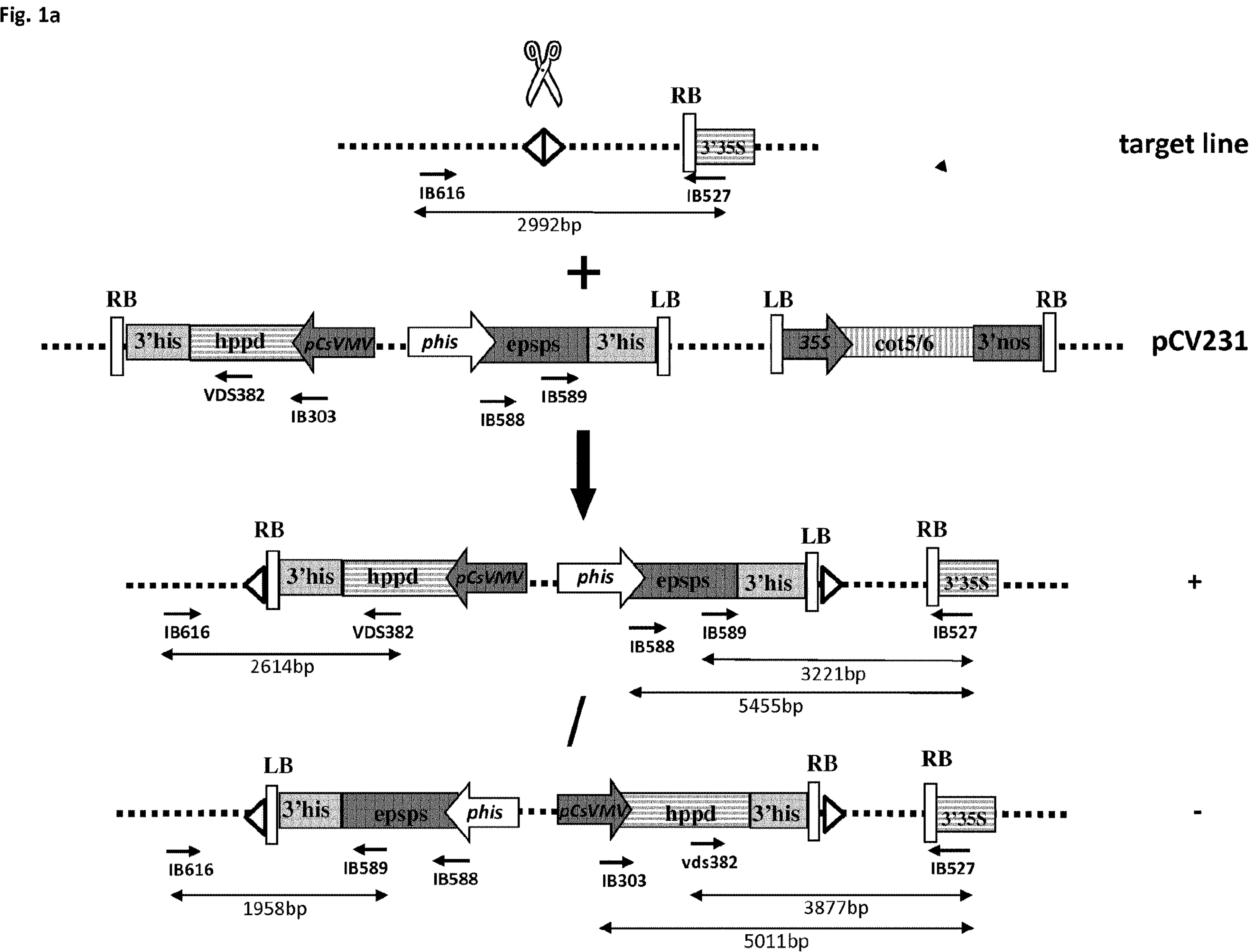

Specification includes a Sequence Listing.

(56) References Cited

U.S. PATENT DOCUMENTS 7,112,665 B1 9/2006 Leemans et al.
7,405,347 B2 7/2008 Hammer et al.
7,659,376 B2 2/2010 Hammer et al.
7,700,842 B2 4/2010 Hammer
7,807,881 B2 10/2010 Hammer et al.
7,834,249 B2 11/2010 Schouten et al.
7,888,552 B2 2/2011 Ye et al.
7,935,862 B2 5/2011 Que
7,960,616 B2 6/2011 Heinrichs et al.
7,989,679 B2 8/2011 Koziel et al.
8,003,854 B2 8/2011 Peters et al.
8,148,607 B2 * 4/2012 D'Halluin .......... C12N 15/8201 435/320.1
8,158,856 B2 4/2012 Block et al.
8,765,448 B2 * 7/2014 Rolland ............. C12N 15/8213 435/254.11
9,593,317 B2 3/2017 D'Halluin
2006/0021093 A1 1/2006 Hammer et al.
2006/0021094 A1 1/2006 Hammer et al.
2006/0150269 A1 7/2006 Hammer et al.
2006/0150270 A1 7/2006 Hammer et al.
2006/0253916 A1 11/2006 Biesgen
2007/0004907 A1 1/2007 Hammer et al.
2007/0136840 A1 6/2007 Peters et al.
2007/0289035 A1 12/2007 Berg et al.
2007/0294785 A1 12/2007 Heinrichs
2007/0300326 A1 12/2007 Peters et al.
2008/0182332 A1 7/2008 Cai et al.
2008/0307359 A1 12/2008 Louch et al.
2009/0018016 A1 1/2009 Duck et al.
2009/0089890 A1 * 4/2009 D' Halluin ........ C12N 15/8201 800/266
2009/0119797 A1 5/2009 Hammer et al.
2009/0126044 A1 5/2009 Carozzi et al.
2009/0151018 A1 6/2009 Hammer et al.
2009/0203075 A1 8/2009 Hammer et al.
2009/0227771 A1 9/2009 Peters et al.
2009/0241219 A1 9/2009 Hammer et al.
2009/0313717 A1 12/2009 Hernandez et al.
2010/0071083 A1 3/2010 Smith et al.
2010/0199389 A1 8/2010 Butler et al.
2011/0008833 A1 1/2011 Petolino et al.
2014/0173770 A1 * 6/2014 D'Halluin .......... C12N 15/8213 800/260
2014/0196169 A1 * 7/2014 D'Halluin ............ C12N 9/0069 800/270

FOREIGN PATENT DOCUMENTS

EP 0176112 B1 5/1990
EP 0120516 B1 10/1991
EP 0292435 B1 7/1995
EP 0116718 B2 5/1996
EP 0290799 9/2004
EP 0320500 B1 11/2004
EP 0837944 B1 3/2006
EP 0604662 B1 6/2008
EP 1950303 A1 7/2008
EP 2099905 A1 9/2009
EP 1794306 B1 12/2009
EP 2300618 A1 3/2011
EP 1999141 B1 6/2011
EP 2018431 B1 8/2011
EP 2099915 B1 9/2011
EP 1807519 B1 2/2012
EP 1999263 B1 4/2013
EP 2052077 B1 10/2014
JP 2006304779 A 11/2006
WO 8402919 A1 8/1984
WO 9214827 9/1992
WO 9404692 3/1994
WO 9404693 A 3/1994
WO 9409144 A 4/1994
WO 9507355 3/1995
WO 9513389 A 5/1995
WO 9638567 12/1996
WO 9704103 A2 2/1997
WO 9934008 7/1999
WO 0004173 1/2000
WO 0008175 2/2000
WO 0008184 2/2000
WO 0008185 2/2000
WO 0011192 3/2000
WO 0014249 3/2000
WO 0022140 4/2000
WO 00666746 4/2000
WO 0028052 5/2000
WO 0073422 5/2000
WO 0047727 8/2000
WO 0066747 11/2000
WO 0077229 12/2000
WO 0112782 A2 2/2001
WO 0112826 A2 2/2001
WO 0114569 A2 3/2001
WO 0119975 A2 3/2001
WO 0124615 A1 4/2001
WO 0166704 A2 9/2001
WO 0198509 A2 12/2001
WO 0226995 A1 4/2002
WO 0234923 A2 5/2002
WO 0236782 A2 5/2002
WO 0236787 A2 5/2002
WO 0246387 A2 6/2002
WO 2002079410 A2 10/2002
WO 02101059 A2 12/2002
WO 0300459 A2 1/2003
WO 03013226 A2 2/2003
WO 2003033540 A2 4/2003
WO 03071860 A2 9/2003
WO 03080809 A2 10/2003
WO 03092360 A2 11/2003
WO 2004024928 A2 3/2004
WO 2004040012 A2 5/2004
WO 2004056999 A1 7/2004
WO 2004067736 A2 8/2004
WO 2004078983 A2 9/2004
WO 2004090140 A2 10/2004
WO 2004106529 A2 12/2004
WO 2005002359 A2 1/2005
WO 2005012529 A1 2/2005
WO 2005020673 A1 3/2005
WO 2005030941 A1 4/2005
WO 2005030942 A1 4/2005
WO 2005012515 5/2005
WO 2005049842 A2 6/2005
WO 2005093093 A2 10/2005
WO 2005095617 A2 10/2005
WO 2005095618 A2 10/2005
WO 2005095619 A1 10/2005
WO 2005095632 A2 10/2005
WO 2005123927 A1 12/2005
WO 2006007373 A2 1/2006
WO 2006015376 A2 2/2006
WO 2006018319 A1 2/2006
WO 2006024351 A1 3/2006
WO 2006032469 A2 3/2006
WO 2006032538 A1 3/2006
WO 2006045633 A1 5/2006
WO 2006060634 A2 6/2006
WO 2006063862 A1 6/2006
WO 2006072603 A2 7/2006
WO 2006103107 A1 10/2006
WO 2006105946 A2 10/2006
WO 2006108702 A1 10/2006
WO 2006129204 A2 12/2006
WO 2006133827 A2 12/2006
WO 2007009823 A1 1/2007
WO 2007024782 A2 3/2007
WO 2007035650 A2 3/2007
WO 2007039314 A2 4/2007
WO 2007039315 A1 4/2007
WO 2007039316 A1 4/2007
WO 2007047859 A2 4/2007

(56) References Cited

FOREIGN PATENT DOCUMENTS

| | | | |
|---|---|---|---|
| WO | 2007027777 | B1 | 7/2007 |
| WO | 2007074405 | A2 | 7/2007 |
| WO | 2007080127 | A2 | 7/2007 |
| WO | 2007103567 | A2 | 9/2007 |
| WO | 2007107302 | A2 | 9/2007 |
| WO | 2007107326 | A1 | 9/2007 |
| WO | 2008037436 | A1 | 4/2008 |
| WO | 2007080126 | A9 | 8/2008 |
| WO | 2008148559 | A1 | 12/2008 |
| WO | 2008150473 | A2 | 12/2008 |
| WO | 2009144079 | A1 | 12/2009 |
| WO | 2010079430 | A1 | 7/2010 |
| WO | 2011072246 | A2 | 6/2011 |
| WO | 2011146121 | A1 | 11/2011 |
| WO | 2011154158 | A1 | 12/2011 |
| WO | 2013026740 | A2 | 2/2013 |

OTHER PUBLICATIONS

Miller et al (High efficiency transgene segregation in co-transformed maize plants using an Agrobacterium tumefaciens 2 T-DNA binary system. Transgenic Research 11: 381-396, 2002).*

Hwang et al (Agrobacterium-mediated plant transformation: biology and applications. American Society of Plant Biologists. 1-31, 2017) (Year: 2017).*

Rathore et al (Alternative Non-Agrobacterium Based Methods for Plant Transformation. Annual Plant Reviews. 1, 1-17, 2018) (Year: 2018).*

Lin et al (Efficient linking and transferor multiple genes by a multigene assembly and transformation vector system. PNAS. 100, 6962-5967, 2003) (Year: 2003).*

Muyrers et al, Techniques: Recombinogenic engineering—new options for cloning and manipulating DNA. TRENDS in Biochemical Sciences vol. 26 No. 5, 325-331, 2001 (Year: 2001).*

Lin et al (Efficient linking and transfer of multiple genes by a multigene assembly and transformation vector system. PNAS. 100, 6962-5967, 2003). (Year: 2003).*

Kumar et al. (Stable transformation of the cotton plastid genome and maternal inheritance of transgenes. Plant Molecular Biology 56: 203-216, 2004). (Year: 2004).*

Zhang et al, "High frequency targeted mutagenesis in *Arabidopsis thaliana* using zinc finger nucleases", pp. 12028-12033, PNAS, Jun. 29, 2010, vol. 107, No. 26; www.pnas.org/cgi/doi/10.1073/pnas.0914991107.

An et al., "New cloning vehicles for transformation of higher plants", Institute of Biological Chemistry, The EMBO Journal, vol. 4, No. 2, pp. 277-284, 1985.

Araki et al., "Molecular and Functional Organization of Yeast Plasmid pSR1", J. Mol. Biol. (1985) 182, pp. 191-203.

Broothaerts et al., "Gene transfer to plants by diverse species of bacteria", letters to nature, Cambia, Canberra, AU, Nature |vol. 433 | Feb. 10, 2005 |www.nature.com/nature, 2005, pp. 629-633.

Cai et al., "Targeted transgene integration in plant cells using designed zinc finger nucleases", 2009, Plant Mol Biol., 69: pp. 699-709.

Chen et al., "Controlled Expression of the Transcriptional Activator Gene virG in Agrobacterium tumefaciens by Using the *Escherichia coli* lac Promoter", Section of Microbiology, Cornell University, Ithaca, New York, Journal of Bacteriology, vol. 173, No. 3, Feb. 1991, pp. 1139-1144.

Christian et al. "Targeting DNA Double-Strand Breaks with TAL Effector Nucleases", Dept. of Genetics, University of Minnesota, Minneapolis, MN, Oct. 2010, Genetics 186: pp. 757-761.

Comai, "An Altered aroA Gene Product Confers Resistance to the Herbicide Glyphosate", Science vol. 221, Jul. 22, 1983, pp. 370-371.

Crickmore et al., "Bacillus thuringiensis Toxin Nomenclature:", http://www.lifesci.sussex.ac.uk/home/Neil_Crickmore/Bt/intro.html, Feb. 2, 2011, 6 pages.

Crickmore et al., "Revision of the Nomenclature for the Bacillus thuringiensis Pesticidal Crystal Proteins", Microbiology and Molecular Biology Reviews, Sep. 1998, p. 807-813 vol. 62, No. 3.

D'Halluin et al., "Transgenic Maize Plants by Tissue Electroporation", The Plant Cell, vol. 4, pp. 1495-1505, Dec. 1992, American Society of Plant Physiologists.

Fraley et al., "Genetic Transformation in Higher Plants", vol. 4, Issue 1, Dept. of Biological Sciences, Monsanto Co., St. Louis, Missouri, 1986, CRC Critical Reviews in Plant Sciences, pp. 1-46.

Fraley et al., "The SEV System: A New Disarmed TI Plasmid Vector System for Plant Transformation", Research Papers, Monsanto Company, St. Louis, MO, Bio/Technology, vol. 3, Jul. 1985, pp. 629-635.

Fromm et al., "Expression of Genes Transferred into Monocot and Dicot Plant Cells by Electroporation", PNAS, Proc. Natl. Acad. Sci. USA, vol. 82, pp. 5824-5828, Sep. 1985Genetics.

Gasser, "Structure, Expression, and Evolution of the 5-Enolpyruvylshikimate-3-phosphate Synthase Genes of Petunia and Tomato", The Journal of Biological Chemistry, vol. 263, No. 9, Issue of Mar. 25, St. Louis, Missouri, pp. 4280-4289, 1988.

Gelvin, "Agrobacterium in the Genomics Age", Update on Genomics of Agrobacterium-Mediated Plant Transformation, Plant Physiology, Purdue University, West Lafayette, Indiana, Aug. 2009, vol. 150, pp. 1665-1676.

Gelvin, "Agrobacterium-Mediated Plant Transformation: the Biology behind the "Gene-Jockeying" Tool", Microbiology and Molecular Biology Reviews, Mar. 2003, p. 16-37, vol. 67, No. 1, West Lafayette, Indiana.

Gordon-Kamm et al., "Transformation of Maize Cells and Regeneration of Fertile Transgenic Plants", The Plant Cell, vol. 2, 603-618, Jul. 1990, American Society of Plant Physiologists, Groton, Connecticut.

Groth et al., "A phage integrase directs efficient site-specific integration in human cells", Department of Genetics, Stanford University School of Medicine, Stanford, CA, PNAS, May 23, 2000, vol. 97, No. 11, pp. 5995-6000.

Hiei et al., Efficient transformation of rice (*Oryza sativa* L.) mediated by Agrobacterium and sequence analysis of the boundaries of the T-DNA, The Plant Journal, Shizuoka, Japan, 1994, pp. 271-282.

Hoekema et al., "A binary plant vector strategy based on separation of vir-and T-region of the Agrobacterium tumefaciens Ti-plasmid", Nature vol. May 12, 1983, University of Leiden, The Netherlands, pp. 179-180.

Hood et al., "New Agrobacterium helper plasmids for gene transfer to plants", Transgenic Research 2, Department of Biology, pp. 208-218 (1993).

Hood et al., "The Hypervirulence of Agrobacterium tumefaciens A281 Is Encoded in a Region of pTiBo542 Outside of T-DNA", Journal of Bacteriology, Dec. 1986, p. 1291-1301 vol. 168, No. 3.

Isalan, "A rapid, generally applicable method to engineer zinc fingers illustrated by targeting the HIV-1 promoter", vol. 19, Jul. 2001, Nature Publishing Group http://biotech.nature.com, Medical Research Council Laboratory of Molecular Biology, Hills Road, Cambridge CB2 2QH, UK, pp. 656-660.

Ishida et al., "High efficiency transformation of maize (*Zea mays* L.) mediated by Agrobacterium tumefaciens", Nature Biotechnology, vol. 14, Jun. 1996, Nature Publishing Group http://www.nature.com/naturebiotechnology, pp. 745-750.

Jen et al., "Activity of T-DNA Borders in Plant Cell Transformation by Mini-T Plasmids", Department of Biology, Washington University, St. Louis, Missouri, Journal of Bacteriology, May 1986, vol. 166, No. 2, pp. 491-499.

Kaeppler et al., "Silicon carbide fiber-mediated DNA delivery into plant cells", Plant Cell Reports, 1990, pp. 415-418.

Klein et al., "Transfer of foreign genes into intact maize cells with high-velocity microprojectiles", Proc. Natl. Acad. Sci., USA, vol. 85, pp. 4305-4309, Jun. 1988.

Komari et al., "Vectors carrying two separate T-DNAs for cotransformation of higher plants mediated by Agrobacterium tumefaciens and segregation of transformants free from selection markers", The Plant Journal (1996) 10(1), Shizuoka, Japan, pp. 165-174.

(56) References Cited

OTHER PUBLICATIONS

Komori et al., "Current Status of Binary Vectors and Superbinary Vectors, Update on Binary Vectors", Shizuoka, Japan, Plant Physiology, Dec. 2007, vol. 145, pp. 1155-1160, www.plantphysiol.org, American Society of Plant Biologists.

Koncz et al., "The promoter of TL-DNA gene 5 controls the tissue-specific expression of chimaeric genes carried by a novel type of Agrobacterium binary vector", Mol Gen Genet (1986) 204: pp. 383-396.

Laboratory Press, McPherson at al. (2000) PCR—Basics: From Background to Bench, First Edition, Springer Verlag, Germany.

Lazo et al, "A DNA Transformation-Competent *Arabidopsis* Genomic Library in Agrobacterium", Department of Biology, Sinsheimer Laboratories, University of California, Santa Cruz, CA, Bio/Technology, vol. 9, Oct. 1991, pp. 963-967.

Lee et al., "T-DNA Binary Vectors and Systems", Update on T-DNA Binary Vectors, Plant Physiology, Department of Biological Sciences, Purdue University, West Lafayette, Indiana, Feb. 2008, vol. 146, pp. 325-332, www.plantphysiol.org, 2008, American Society of Plant Biologists.

Liu et al., "Design of polydactyl zinc-finger proteins for unique addressing within complex genomes", Proc. Natl. Acad. Sci, USA, vol. 94, pp. 5525-5530, May 1997, Biochemistry.

Lloyd et al., "Targeted mutagenesis using zinc-finger nucleases in *Arabidopsis*", Salt Lake City, Utah, pp. 2232-2237 PNAS Feb. 8, 2005, vol. 102, No. 6, www.pnas.orgcgidoi10.1073pnas.0409339102.

Moellenbeck et al., "Insecticidal proteins from Bacillus thuringiensis protect corn from corn rootworms", 2001 Nature Publishing Group http://biotech.nature.com, nature biotechnology • vol. 19 • Jul. 2001 • http://biotech.nature.com, pp. 668-672.

Needleman et al., "A General Method Applicable to the Search for Similarities in the Amino Acid Sequence of Two proteins", Department of Biochemistry, Northwestern University, Chicago, IL, J. Mol. Biol., 1970, 48, pp. 443-453.

Paszkowski et al., "Direct gene transfer to plants", The EMBO Journal, vol. 3, No. 12, pp. 2717-2722, 1984, Basel, Switzerland.

Potrykus et al., "Molecular and general genetics of a hybrid foreign gene introduced into tobacco by direct gene transfer", Mol Gen Genet (1985) 99: pp. 169-177, Basel, Switzerland.

Rogers, "Improved Vectors for Plant Transformation", Methods in Enzymology, vol. 153, 1987, pp. 253-277.

Sambrook et al., (2001) Molecular Cloning: A Laboratory Manual, Third Edition, Cold Spring Harbor Laboratory Press, NY.

Scheeren-Groot et al., "Mutational Analysis of the Transcriptional Activator VirG of Agrobacterium tumefaciens", Journal of Bacteriology, Nov. 1994, p. 6418-6426 vol. 176, No. 21, AL Leiden, The Netherlands.

Schnepf et al., "Characterization of Cry34/Cry35 Binary Insecticidal Proteins from Diverse Bacillus thuringiensis Strain Collections", Applied and Environmental Microbiology, Apr. 2005, p. 1765-1774 vol. 71, No. 4, Indianapolis, Indiana.

Shah et al., "Engineering Herbicide Tolerance in Transgenic Plants", Science, vol. 233, Jul. 25, 1986, pp. 478-481.

Shimamoto et al., "Fertile transgenic rice plants regenerated from transformed protoplasts", Letters to Nature, Plantech Research Institute, Yokohama, Japan, vol. 338, Mar. 16, 1989, pp. 274-276.

Shukla et al., "Precise genome modification in the crop species *Zea mays* using zinc-finger nucleases", vol. 459, May 21, 2009, doi:10.1038, nature07992, Macmillan Publishers Limited, pp. 437-443.

Thorpe et al., "In vitro site-specific integration of bacteriophase DNA catalyzed by a recombinase of the resolvase/invertase family", Proc. Natl. Acad. Sci. USA, vol. 95, pp. 5505-5510, May 1998, Biochemistry.

Tranel, "Resistance of weeds to ALS-inhibiting herbicides: what have we learned?", Weed Science, 50: pp. 700-712. 2002.

Tzfira et al., "Agrobacterium-mediated genetic transformation of plants: biology and biotechnology", Elsevier, Science Direct, Current Opinion in Biotechnology 2006, 17: pp. 147-154.

Wright et al., "High-frequency homologous recombination in plants mediated by zinc-finger nucleases", The Plant Journal, USA, 2005 Blackwell Publishing Ltd, 44, pp. 693-705, doi: 10.1111/j.1365-313X.2005.02551.x.

Chilton, et al., "Targeted Integration of T-DNA into the Tobacco Genome at Double-Stranded Breaks: New Insights on the Mechanism of T-DNA Integration", Plant Physiology, vol. 133, Issue 3, Nov. 2003, pp. 956-965.

Matthews, et al., "Marker gene elimination from transgenic barley, using co-transformation with adjacent 'twin T-DNAs' on a standard Agrobacterium transformation vector", Molecular Breeding, vol. 7, Issue 3, Sep. 2001, pp. 195-202.

Xing, et al., "The use of the two T-DNA binary system to derive marker-free transgenic soybeans", In Vitro Cellular & Developmental Biology—Plant, vol. 36, Issue 6, Nov. 2000, pp. 456-463.

Interlocutory Decision in Opposition Proceedings for European Patent Application No. 13717522.0 dated Mar. 27, 2020.

* cited by examiner

Fig. 2a

3'flanking seq

Cot5/6 cleavage site

```
stacked event   2068 ttgtttaatatgaattttgagagcactatttttatgccgtgcctaattaaaattatttacggcaggatatattcaattgtaaatggctc
cons.93-23      2067 ttgtttaatatgaattttgagagcactatttttatgccgtgcctaattaaaatt-------------tgatgtcaattgtaaatggctc
cons.91-74      2068 ttgtttaatatgaattttgaaggcactatttttatgccgtgcct---------------------------------------------
cons.92-13      2070 ttgtttaatatgaattttgagagcactatttttatgccgtgcctaattaaaatta------------------------taaatggctc

stacked event   2158 catggcgatcgctacaaccaaactgtctcacgacgttttgataacttcgtataatgtatgctatacgaagttatgttcccgatcaaatc
cons.93-23      2143 catggcgatcgctacaaccaaactgtctcacgacgttttgataacttcgtataatgtatgctatacgaagttatgttcccgatcaaatc
cons.91-74           -----------------------------------------------------------------------------------------
cons.92-13      2135 catggcgatcgctacaaccaaactgtctcacgacgttttgataacttcgtataatgtatgctatacgaagttatgttcccgatcaaatc

stacked event   2248 tgagggacgttaaagcgatgataaattggaaccagaatatagaatctttgttctgctctagcttttcttctgtacatttttacgattag
cons.93-23      2233 tgagggacgttaaagcgatgataaattggaaccagaatatagaatctttgttctgctctagcttttcttctgtacatttttacgattag
cons.91-74      2112 -----------------------aattggaaccagaatatagaatctttgttctgctctagcttttcttctgtacatttttacgattag
cons.92-13      2225 tgagggacgttaaagcgatgataaattggaaccagaatatagaatctttgttctgctctagcttttcttctgtacatttttacgattag
```

Fig. 2b

Extra seq inserted=(lox-I-creI-LB)

Cot5/6 cleavage site

3'flanking seq

```
stacked event  1571 atgaaaatcatagtctaatcgtaaaaaatgtacagaagaaaagctagagcagaacaaagattctatattctggttccaatttatcatcgctttaacgtcc
91-74a         1033 atgaaaatcatagtctaatcgtaaaaaatgtacagaagaaaagctagagcagaacaaagattctatattctggttccaatttatcatcgctttaacgtcc
91-74b          498 atgaaaatcatagtctaatcgtaaaaaatgtacagaagaaaagctagagcagaacaaagattctatattctggttccaatttatcatcgctttaacgtcc
92-13          1124 atgaaaatcatagtctaatcgtaaaaaatgtacagaagaaaagctagagcagaacaaagattctatattctggttccaatttatcatcgctttaacgtcc

stacked event  1671 ctcagatttgatcggg------------------ccttaattaacccgggcctgcaggtcgacggccga-------gtactggca---------gga----
91-74a          933 ctcagatttgatcggg------------------ccttaattaacccgggcctgcaggtcgacggccga-------g-----------------------
91-74b          398 ctcagatttgatcggg------------------ccttaattaacccgggcctgcaggtcgacggccga-------gtac--------------------
92-13          1024 ctcagatttgatcgggaaacataacttcgtatagcatacattatacgaagttatcaaaacgtcgtgagacagtttggttgtagcgatcgccatggagcca

stacked event  1734 --tatataccgtt----gtaattaagtgtttatgttgatattttaattatgtttcatataaatttgtcgtaatagtttaattgttaaatctaaataaaag
91-74a          881 -------------------------------------------------ttatgtttcatataaatttgtcgtaatagtttaattgttaaatctaaataaaag
91-74b              ----------------------------------------------------------------------------------------------------
92-13           924 tttacaaactgtctcaagttatcaagtgtttatgttgatattttaattatgtttcatataaatttgtcgtaatagtttaattgttaaatctaaataaaag

stacked event  1828 tatttaaaaatagatattatatttttatgatatatataaatatcatgaaactttagaatttatggacaaaaacatcactatccactagttaatcatttc
91-74a          827 tatttaaaaatagatattatatttttatgatatatataaatatcatgaaactttagaatttatggacaaaaacatcactatccactagttaatcatttc
91-74b              ----------------------------------------------------------------------------------------------------
92-13           824 tatttaaaaatagatattatatttttatgatatatataaatatcatgaaactttagaatttatggacaaaaacatcactatccactagttaatcatttc

stacked event  1928 tacaaacgacatttatttatttaaaatggtcagaaaaattgtgacctaccaggaatgaggatttgattggagggatgtaaaccaagttgatatttttttc
91-74a          727 tacaaacgacatttatttatttaaaatggtcagaaaaattgtgacctaccaggaatgaggatttgattggagggatgtaaaccaagttgatatttttttc
91-74b              ----------------------------------------------------------------------------------------------------
92-13           724 tacaaacgacatttatttatttaaaatggtcagaaaaattgtgacctaccaggaatgaggatttgattggagggatgtaaaccaagttgatatttttttc

stacked event  2028 tcacttgtgaaaaagatagtgtttggctggaattttatgtatgataaatttgatagggacttgcacttgagattatttctgggttcttcatgcttttat
91-74a          627 tcacttgtgaaaaagatagtgtttggctggaattttatgtatgataaatttgatagggacttgcacttgagattatttctgggttcttcatgcttttat
91-74b              ----------------------------------------------------------------------------------------------------
92-13           624 tcacttgtgaaaaagatagtgtttggctggaattttatgtatgataaatttgatagggacttgcacttgagattatttctgggttcttcatgcttttat

stacked event  2128 aataacttgactatcaaattctctctttggattctacgacgttcatatctatttgtatggtggcttcgagtaggaatttttttaaaagtatttgtgtttg
91-74a          527 aataacttgactatcaaattctctctttggattctacgacgttcatatctatttgtatggtggcttcgagtaggaatttttttaaaagtatttgtgtttg
91-74b          343 ---------------------------tggataataggac-------------------------------------------------------tgg
92-13           524 aataacttgactatcaaattctctctttggattctacgacgttcatatctatttgtatggtggcttcgagtaggaatttttttaaaagtatttgtgtttg

stacked event  2228 atatttacatatgtttttatacaatgtttagaactacttatagtccatttcatcccttaagtaggtacgccttcctacattgacaacaatatcgatacta
91-74a          427 atatttacatatgtttttatacaatgtttagaactacttatagtccatttcatcccttaagtaggtacgccttcctacattgacaacaatatcgatacta
91-74b          327 atatttacatat----------------------------------------------------------------------------------------
92-13           424 atatttacatatgtttttatacaatgtttagaactacttatagtccatttcatcccttaagtaggtacgccttcctacattgacaacaatatcgatacta

stacked event  2328 atcgaactaaaactcaatcaacgcccatattcgacacttcaatttggataataagtagagtattttatagatatttgatttatatgtaaatgatttttt
91-74a          327 atcgaactaaaactcaatcaacgcccatattcgacacttcaatttggataataagtagagtattttatagatatttgatttatatgtaaatgatttttt
91-74b          315 ------ttaaaactcaatcaacgcccatattcgacacttcaatttggataataagtagagtattttatagatatttgatttatatgtaaatgatttttt
92-13           324 atcgaactaaaactcaatcaacgcccatattcgacacttcaatttggataataagtagagtattttatagatatttgatttatatgtaaatgatttttt
```

TARGETED GENOME ENGINEERING IN PLANTS

CROSS-REFERENCE TO RELATED APPLICATIONS

This application is a § 371 U.S. National Stage of International Application No. PCT/EP13/058264, filed Apr. 22, 2013, which claims the benefit of European Patent Application Serial No. 12165201.0, filed Apr. 23, 2012 and U.S. Patent Application Ser. No. 61/636,882, filed Apr. 23, 2012, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS12-2004-WO1_ST25.TXT", created on Apr. 19, 2013, and having a size of 54 kilobytes and is filed concurrently with the specification. The sequence listing contained in this ASCII formatted document is part of the specification and is herein incorporated by reference in its entirety.

FIELD OF THE INVENTION

The invention relates to the field of agronomy. More particularly, the invention provides methods and means to introduce a targeted modification, including insertion, deletion or substitution, at a precisely localized nucleotide sequence in the genome of a plant cell or plant via bacterium-mediated transformation, such as *Agrobacterium*. The modifications are triggered in a first step by induction of a double stranded break at a recognition nucleotide sequence using a double stranded DNA break inducing enzyme encoded by a T-DNA which has been introduced into the plant cell, while a co-introduced T-DNA comprising a repair DNA molecule is subsequently used as a template for repair of the double stranded break. The frequency of correctly targeted genome modification is increased by co-introduction of the two T-DNA molecules by a single bacterium cell.

BACKGROUND

*Agrobacterium* mediated DNA transfer is the standard method of transformation for most plants, including crop plants. The advantages of the *Agrobacterium* method over other methods include the high efficiency of transformation, the transfer of pieces of DNA with defined ends, the transfer of relatively large segments of DNA, and the absence of a requirement for protoplast culture techniques (Komari et al., 1996 Plant J. 10: 165-174).

When more than one construct is to be transformed, direct DNA delivery methods such as particle bombardment or electroporation may be more efficient because of a higher frequency of cotransformation compared to the simultaneous transformation with more than one *Agrobacterium* strains. However, a disadvantage of these direct delivery methods is that they can lead to more complex transgene integration patterns, making the identification of single copy transformants lengthy and laborious process.

In order to be able to introduce a foreign DNA at a predetermined site, so-called gene targeting, it is required to transform plants cells or tissues with two constructs, one comprising a gene encoding an enzyme that induces a double stranded DNA break (DSB) at a specific target site and one comprising a DNA of interest for repair of the break. This process may also be more efficient when plant cells are transformed with the repair DNA and the DNA encoding the double stranded DNA break inducing (DSBI) enzyme simultaneously using direct DNA delivery methods, than when using two *Agrobacterium* strains.

The frequency of DSB induction and subsequent repair using DNA of interest via *Agrobacterium*-mediated transformation can be improved by co-delivery of the repair DNA and DSBI enzyme encoding gene on the same T-DNA using a single *Agrobacterium* strain. However, this can lead to co-integration of the DSBI enzyme encoding gene at the site of double strand break induction, which is undesirable. This co-integration can be avoided by constructing the T-DNA vector in a way that that the DNA to be introduced into the genome is flanked by regions having homology to the genomic target site, thereby directing insertion via homologous recombination, but whereby the DSBI gene is located outside of these homology regions, but cloning procedures become more complicated because additional elements need to be included in one construct.

Wright et al. (2005, plant J, 44:693-705) discloses Zinc finger nuclease (ZNF) induced chromosomal break repair at an engineered target locus via homologous recombination in tobacco protoplast by simultaneous electroporation of two linearized plasmids containing the ZNF expression construct and donor DNA respectively.

Shukla et al. (2009, Nature 459: 437-441), U.S. Ser. No. 08/018,2332 and U.S. Ser. No. 10/019,9389 describe targeted insertion into an endogenous locus in maize by codelivery of designed ZNF expression constructs with donor plasmids containing homology arms into maize embryogenic cell cultures via Whiskers and particle bombardment.

Lloyd et al. (2005, Proc Natl Acad Sci, 102: 2232-2237) and Zhang et al. (2009, Proc Natl Acad Sci, 107: 12028-1203) and U.S. Ser. No. 10/007,1083 describe an inducible DSBI enzyme encoding gene that has been stably transformed into the plants genome for use in targeted mutagenesis.

Cai et al. (2009, Plant Mol Biol, 69: 699-709) and US2011008833 describe homology mediated targeted insertion into engineered and endogenous tobacco loci using *Agrobacterium*, via co-culture of two *Agrobacterium* strains of which one harbors a donor DNA and the other a designed ZNF expression construct, but also by co-culturing with a single *Agrobacterium* strain containing a Ti plasmid harboring both the ZNF and donor construct within the same T-DNA.

Komari et al. (1996, Plant J 10: 165-174) and U.S. Pat. No. 5,731,179 discloses super-binary vectors for producing transformants free from selection markers.

Thus, in view of the advantages of the *Agrobacterium* system for plant transformation, the need remains for more efficient methods for the co-delivery of the repair DNA molecule and the DSBI enzyme encoding chimeric gene using *Agrobacterium*. This problem is solved hereinafter, in the detailed description, examples and claims.

FIGURE LEGENDS

Figure 1B:
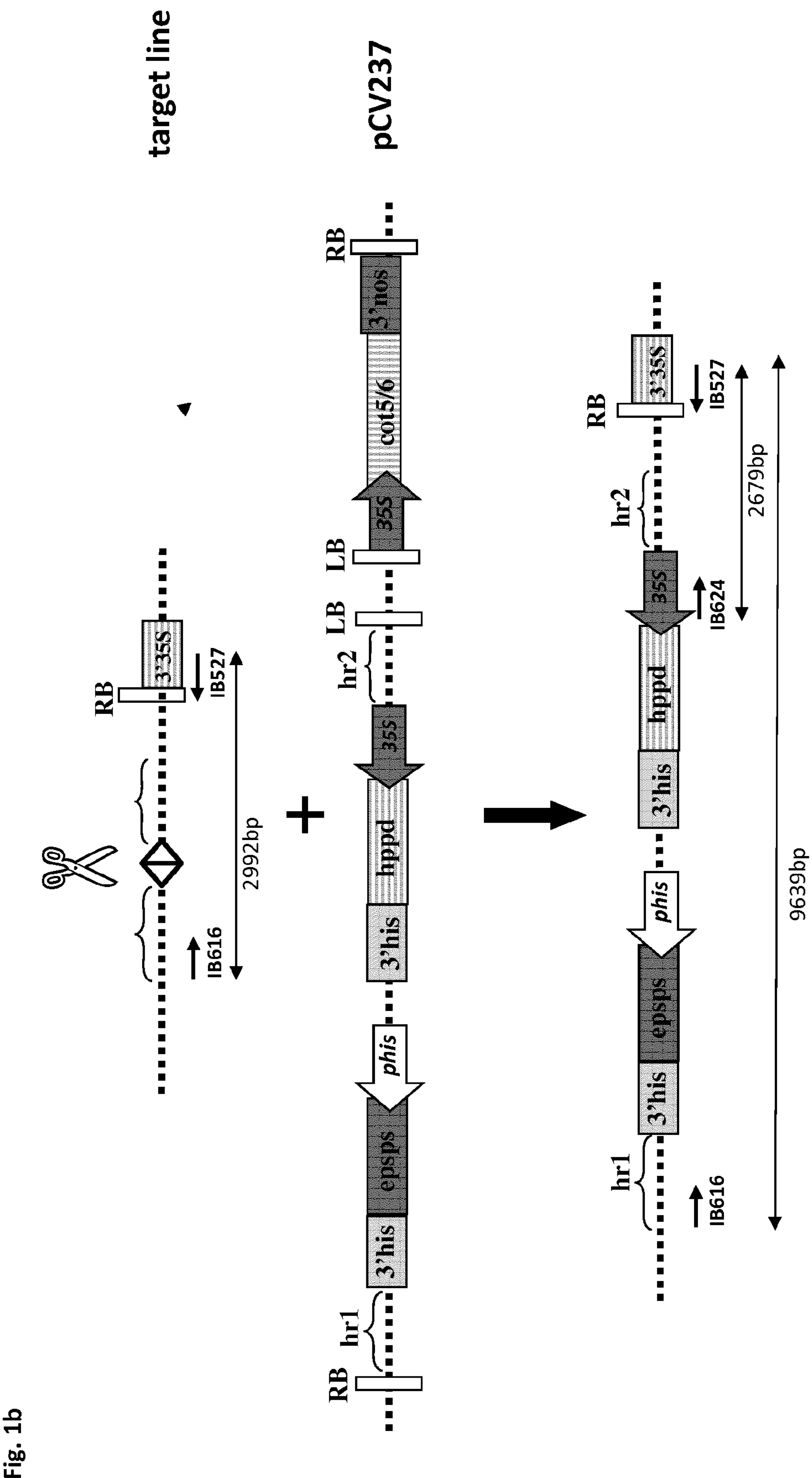

FIG. 1: (a) Schematic representation of targeted insertion into a preselected genomic target site using a dual T-DNA vector comprising a repair DNA molecule with a DNA of interest (chimeric genes encoding 2mEPSPS and Pf-HPPD) between one set of T-DNA borders and a chimeric gene encoding an endonuclease recognising a recognition site in the genome of the target plant between a second pair of T-DNA borders. The outcome of non-homology based targeted insertion are two possible events, depending on the orientation of the inserted DNA of interest (random). Primers and their amplification products for identification of the events are indicated. The scissors represent the meganuclease protein, which induces a break at its recognition site indicated by the two triangles (each triangle representing one half-part recognition site). RB and LB stands for right and left T-DNA border respectively. (b): Similar situation as in a), but here the repair DNA additionally comprises DNA regions flanking the DNA of interest (homology regions 1 and 2: hr1 and hr2, indicated by accolades) which have homology to respectively the region upstream or the region downstream of the preselected site/recognition site, also indicated by accolades. In this scenario, the orientation of the insert is not random but is determined by the homology of hr1 and h2 to either the region upstream or downstream of the predefined site. Also depending on the choice of the homology regions, the half-part recognition sites remain or do not remain in the genome.

FIG. 2: Sequence alignment of candidate correctly targeted insertion events. (a) right side insertion events (stacked event (SEQ ID NO:12); cons. 93-23 (SEQ ID NO:13), cons. 91-74 (SEQ ID NO:14); and cons. 92-13 (SEQ ID NO:15), (b) left side insertion events (stacked event (SEQ ID NO:16); 91-74a (SEQ ID NO:17), 91-74b (SEQ ID NO:18), and 92-13 (SEQ ID NO:19).

DETAILED DESCRIPTION

In previous experiments, co-transformation of a repair DNA and a DSBI enzyme encoding DNA resulted in a frequency of correctly targeted insertion events was about ten times higher when using direct DNA delivery methods (e.g. particle bombardment) than when co-incubating with two *Agrobacterium* strains. The present invention is based on the finding that the frequency of targeted insertion events whereby a repair DNA and a DNA encoding a DSBI enzyme are co-delivered to plants cells via *Agrobacterium* can be increased up to a similar frequency as when using direct DNA delivery methods, when the cells are transformed with a single *Agrobacterium* strain comprising the two DNA molecules in separate T-DNAs, e.g. on the same T-DNA vector (a dual T-DNA vector). This improved method of co-delivery of the DSBI enzyme encoding gene and repair DNA via *Agrobacterium* transformation thus combines the advantages of *Agrobacterium*-mediated transformation with a frequency of targeted genome modifications equal to that of direct delivery methods, while at the same time permitting any integrated DSBI enzyme encoding gene to be segregated from the targeted modification in the next generation.

Thus, in a first embodiment, the invention relates to a method for modifying the genome of a plant cell at a preselected site, comprising the steps of:

a. Contacting a plant cell with a bacterium capable of directing the transfer of defined DNA molecules from said bacterium into the genome of said plant cell, said bacterium comprising:
   i. a first defined DNA molecule comprising a chimeric gene encoding a plant-functional DSBI enzyme, said DSBI enzyme being capable of recognizing and inducing a double stranded DNA break at a recognition site located at or in the vicinity of said preselected site, said chimeric gene comprising the following operably linked elements:
      1. a plant expressible promoter;
      2. a DNA region encoding a DSBI enzyme;
      3. a plant-functional 3' termination and polyadenylation region; and
   ii. a second defined DNA molecule comprising a repair DNA molecule for use as a template for repair of said double stranded DNA break;
b. Selecting a plant cell wherein said repair DNA has been used as a template for repair of the double stranded DNA break, said repair of said double stranded DNA break resulting in a modification of said genome at said preselected site, wherein said modification is selected from
   i. a replacement of at least one nucleotide;
   ii. a deletion of at least one nucleotide;
   iii. an insertion of at least one nucleotide; or
   iv. any combination of i.-iii.

As used herein, a "double stranded DNA break inducing enzyme" is an enzyme capable of inducing a double stranded DNA break at a particular nucleotide sequence, called the "recognition site". Rare-cleaving endonucleases, are DSBI enzymes that have a recognition site of 14 up to 40 or even up to 70 consecutive nucleotides, and therefore have a very low frequency of cleaving, even in the larger plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A list of other rare cleaving meganucleases and their respective recognition sites is provided in Table I of WO 03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I.

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as Fokl. Such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530). Custom-made meganucleases can be produced by selection from a library of variants, is described in WO2004/067736. Custom made meganucleases with altered sequence specificity and DNA-binding affinity may also be obtained through rational design as described in WO2007/047859. Another example of custom-designed endonucleases include the so-called TALE nucleases, which are based on transcription activator-like effectors (TALEs) from the bacterial genus *Xanthomonas* fused to the catalytic domain of a nuclease, e.g. FOKI. The DNA binding specificity of these TALEs is defined by repeat-variable diresidues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al., 2009, Science 326: p 1509-1512; Moscou and Bogdanove, 2009, Science 326: p 1501; Christian et al., 2010, Genetics 186: 757-761, WO10/079430, WO11/072246, WO2011/154393, WO11/146121, WO2012/001527, WO2012/093833, WO2012/104729, WO2012/138927, WO2012/138939). WO2012/138927 further describes monomeric (compact) TALENs and TALENs with various catalytic domains and combinations thereof. Recently, a new type of customizable endonuclease system has been described; the so-called CRISPR/Cas system, which employs a special RNA molecule (crRNA) conferring sequence specificity to guide the cleavage of an associated nuclease Cas9 (Jinek et al, 2012, Science 337:p 816-821). Such custom designed endonucleases are also referred to as non-naturally occurring endonucleases.

Site specific recombinases are enzymes different from endonucleases, but can also be used to carry out the methods of the invention. In contrast to endonucleases, site-specific recombinases require two recognition sites, between which recombination occurs. Thus, a repair DNA comprising at least one such recognition site can be targeted to a genomic locus also comprising at least one such sites. Examples of site-specific recombinases are well known in the art and include for instance the Cre-Lox system from bacteriophage P1 (Austin et al., 1981, Cell, 25:729-736), the Flp-Frt system from *Saccharomyces cerevisiae* (Broach et al., 1982, Cell, 29:227-234), the R-RS system from *Zygosaccharomyces rouxii* (Araki et al., 1985, J. MoL Biol., 182: 191-203) and the integrase from the *Streptomyces* phage PhiC31 (Thorpe & Smith, 1998, Proc. Natl. Acad. Sci., 95: 5505-5510; Groth et al., 2000, Proc. Natl. Acad. Sci., 97: 5995-6000).

As used herein “a preselected site” or “predefined site” indicates a particular nucleotide sequence in the plant genome (e.g. the nuclear genome) at which location it is desired to insert, replace or delete one or more nucleotides. This can e.g. be an endogenous locus or a particular nucleotide sequence in a previously introduced foreign DNA or transgene.

As used herein “at or near said preselected site”, with respect to the location of the recognition site for the DSBI enzyme, refers to the recognition site overlapping with the preselected site (at) or being located further away (in the vicinity of) from the preselected site. This can be e.g. 10 bp, 20 bp, 30 bp, 40 bp, 50 bp from the preselected site, but also e.g. 100 bp, 200 bp, 300 bp, 400 bp, 500 bp, 1 kb, 2 kb or 5 kb. A person skilled in the art would be able to either choose a double stranded DNA break inducing (“DSBI”) enzyme recognizing a recognition site at or near the preselected site or engineer such a DSBI enzyme. Alternatively, a DSBI enzyme recognition site may be introduced into the plant genome using any conventional transformation method or by conventional breeding using a plant line having a DSBI enzyme recognition site in its genome, and any desired DNA may afterwards be introduced into or near that recognition site.

Non-bacteria-based gene transfer and transfection methods, also referred to as direct DNA delivery methods are described in e.g. US2011008833, include but are not limited to, protoplast transfection through calcium-, polyethylene glycol (PEG)- or electroporation-mediated uptake of naked DNA (see Paszkowski et al. (1984), *EMBO J* 3:2717-2722; Potrykus et al. (1985), *Molec. Gen. Genet.* 199:169-177; From et al. (1985), *Proc. Natl. Acad. Sci. USA* 825824-5828; and Shimamoto (1989), *Nature* 338:274-276) and electroporation of plant tissues (D’Halluin et al. (1992), *Plant Cell* 4:1495-1505). Additional methods for plant cell transfection include microinjection, silicon carbide-mediated DNA uptake (Kaeppler et al. (1990), *Plant Cell Reporter* 9:415-418), and microprojectile bombardment (see Klein et al. (1988), *Proc. Natl. Acad. Sci. USA* 85:4305-4309; and Gordon-Kim et al. (1990), *Plant Cell* 2:603-618).).

Bacteria that can be used to carry out the invention can be any bacterium, preferably non-pathogenic or disarmed (not containing oncogenes), that is capable of directing the transfer of defined DNA fragments contained within the bacterium stably into the genome of a plant cell. Such bacteria harbor one or more plasmids, e.g. a tumor-inducing plasmid (Ti plasmid) or a root-inducing plasmid (Ri plasmid), of which the so-called transfer DNA (T-DNA) is transferred into the plant cell and incorporated into the plant genome following transformation. Certain soil bacteria of the order of the Rhizobiales have this capacity, such as Rhizobiaceae (e.g. *Rhizobium* spp., *Sinorhizobium* spp., *Agrobacterium* spp); Phyllobacteriaceae (e.g. *Mesorhizobium* spp., *Phyllobacterium* spp.); Brucellaceae (e.g. *Ochrobactrum* spp.); Bradyrhizobiaceae (e.g. *Bradyrhizobium* spp.), and Xanthobacteraceae (e.g. *Azorhizobium* spp.), *Agrobacterium* spp., *Rhizobium* spp., *Sinorhizobium* spp., *Mesorhizobium* spp., *Phyllobacterium* spp. *Ochrobactrum* spp. and *Bradyrhizobium* spp., examples of which include *Ochrobactrum* sp., *Rhizobium* sp., *Mesorhizobium loti, Sinorhizobium meliloti*. Examples of Rhizobia include *R. leguminosarum* bv, *trifolii, R. leguminosarum* bv, *phaseoli* and *Rhizobium leguminosarum*, bv, *viciae* (U.S. Pat. No. 7,888,552).

Other bacteria that can be employed to carry out the invention which are capable of transforming plants cells and induce the incorporation of foreign DNA into the plant genome are bacteria of the genera *Azobacter* (aerobic), *Closterium* (strictly anaerobic), *Klebsiella* (optionally aerobic), and *Rhodospirillum* (anaerobic, photosynthetically active). Transfer of a Ti plasmid was also found to confer tumor inducing ability on several Rhizobiaceae members such as *Rhizobium trifolii, Rhizobium leguminosarum* and *Phyllobacterium myrsinacearum*, while *Rhizobium* sp. NGR234, *Sinorhizobium meliloti* and *Mesorhizobium loti* could indeed be modified to mediate gene transfer to a number of diverse plants (Broothaerts et al., 2005, Nature, 433:629-633).

The mechanism of T-DNA transfer to plant cells by *Agrobacterium* and the like has been well documented (see e.g. Tzfira and Citovsky (2006) Curr. Opin. Biotechnol. 17: 147-154; Gelvin (2003) Microbiol. Molec. Biol. Rev. 67: 16-37; Gelvin (2009) Plant Physiol. 150: 1665-1676). Briefly, the T-DNA is delimited by two border regions, referred to as right border (RB) and left border (LB). The borders are nicked by virulence protein VirD2 which produces single stranded transferred DNA (the “T-strand”) with covalent attachment of the 40 VirD2 on its 5' end. The protein-DNA complex, also including *Agrobacterium* VirE2 protein, exits *Agrobacterium* cells through the so-called Type 4 secretion system (T4SS, both virulence protein and ssDNA transporter), and is transferred into plant cells and integrated in the plant genome with the help of both *Agrobacterium* virulence proteins and plant factors. The vir genes are normally found as a series of operons on the Ti or Ri plasmids. Various Ti and Ri plasmids differ somewhat in the complement of vir genes, with, for example, virF not always being present. The use of *Agrobacterium*-mediated vectors to introduce DNA into plant cells is well known in the art. See, for example, Fraley et al., (1985; Biotechnology 3: 629-635), Rogers et al., (1987; Methods Enzymol 153: 253-277) and U.S. Pat. No. 5,563,055.

The LB is not strictly required for T-DNA transfer, as oncogene containing T-DNAs lacking the LB but containing the RB were highly virulent whereas such T-DNAs containing the LB but not the RB were completely avirulent (Jen et al., 1986, J Bacteriol 166:491-499). Thus, a T-DNA, as used herein, refers to a DNA molecule that is transferable to a plant cell by a bacterium, which comprises in addition to the DNA to be used for repair of the DNA break (the repair DNA) at least one T-DNA border, preferably at least the right T-DNA border. However, to prevent incorporation of undesired vector elements, the left and the right border should both be included, i.e flanking the DNA of interest, as these define the ends of the T-DNA molecules.

It has been described that the left border is more prone to "read through" than the right border (ref). Thus, in order to reduce the chance of two DNAs in one vector being processed as a single T-DNA molecule, the two T-DNAs can be oriented such that at the point on the vector where the two T-DNAs are located closest to each other, there are no two left borders facing each other (head to head; RB-LB; LB-RB). Thus, in one embodiment, the orientation of the two T-DNAs on the vector is such that at the point on the vector where the two T-DNAs are located closest to each other, there are two right borders facing each other (the T-DNAs are in a tail to tail orientation: LB-RB; RB-LB). In a more preferred embodiment, the orientation of the two T-DNAs on the vector is in the same direction, such that the left border of the one T-DNA faces the right border of the other T-DNA, i.e the two T-DNAs are in a head to tail orientation (LB-LB; RB-LB).

Examples of the bacterium belonging to the genus *Agrobacterium* which may be employed for the invention include but is not limited to *Agrobacterium tumefaciens, Agrobacterium rhizogenes, Agrobacterium radiobacter, Agrobacterium rubi, Agrobacterium vitis*. The *Agrobacterium* species used can be a wild type (e.g., virulent) or a disarmed strain. Suitable strains of *Agrobacterium* include wild type strains (e.g., such as *Agrobacterium tumefaciens*) or strains in which one or more genes is mutated to increase transformation efficiency, e.g., such as *Agrobacterium* strains wherein the vir gene expression and/or induction thereof is altered due to the presence of mutant or chimeric virA or virG genes (e.g. Chen and Winans, 1991, J. Bacteriol. 173: 1139-1144; and Scheeren-Groot et al., 1994, J. Bacteriol. 176:6418-6246), *Agrobacterium* strains comprising an extra virG gene copy, such as the super virG gene derived from pTiBo542, preferably linked to a multiple-copy plasmid, as described in U.S. Pat. No. 6,483,013, for example. Other suitable strains include, but are not limited to: *A. tumefaciens* GV3101 (pMP90)) (Konc and Schell, 1986, Mol Gen Genet. 204:383-396)., LBA4404 (Hoekema et al., Nature 303: 179-180 (1983)); EHA101 (Hood et al., J. Bac. 168: 1291-1301 (1986)); EHA105 (Hood et al., Trans Res. 2: 208-218 (1993)); AGL1 (Lazo et al., Bio Technology 2: 963-967 (1991)).

For *Agrobacterium*-mediated plant transformation, the DNA to be inserted into the plant cell can be cloned into special plasmids, for example, either into an intermediate (shuttle) vector or into a binary vector. Intermediate vectors are not capable of independent replication in *Agrobacterium* cells, but can be manipulated and replicated in common *Escherichia coli* molecular cloning strains. Such intermediate vectors comprise sequences are commonly framed by the right and left T-DNA border repeat regions, that may include a selectable marker gene functional for the selection of transformed plant cells, a cloning linker, a cloning polylinker, or other sequence which can function as an introduction site for genes destined for plant cell transformation. Cloning and manipulation of genes desired to be transferred to plants can thus be easily performed by standard methodologies in *E. coli*, using the shuttle vector as a cloning vector. The finally manipulated shuttle vector can subsequently be introduced into *Agrobacterium* plant transformation strains for further work. The intermediate shuttle vector can be transferred into *Agrobacterium* by means of a helper plasmid (via bacterial conjugation), by electroporation, by chemically mediated direct DNA transformation, or by other known methodologies. Shuttle vectors can be integrated into the Ti or Ri plasmid or derivatives thereof by homologous recombination owing to sequences that are homologous between the Ti or Ri plasmid, or derivatives thereof, and the intermediate plasmid. This homologous recombination (i.e. plasmid integration) event thereby provides a means of stably maintaining the altered shuttle vector in *Agrobacterium*, with an origin of replication and other plasmid maintenance functions provided by the Ti or Ri plasmid portion of the co-integrant plasmid. The Ti or Ri plasmid also comprises the vir regions comprising vir genes necessary for the transfer of the T-DNA. The plasmid carrying the vir region is commonly a mutated Ti or Ri plasmid (helper plasmid) from which the T-DNA region, including the right and left T-DNA border repeats, have been deleted. Such pTi-derived plasmids, having functional vir genes and lacking all or substantially all of the T-region and associated elements are descriptively referred to herein as helper plasmids.

T-DNA vectors for plant transformation can also be prepared using the so-called superbinary system. This is a specialized example of the shuttle vector/homologous recombination system (reviewed by Komari et al, (2006) In: Methods in Molecular Biology (K. Wang, ed.) No. 343: *Agrobacterium* Protocols (2nd Edition, Vol. 1) HUMANA PRESS Inc., Totowa, N.J., pp. 15-41; and Komori et al, (2007) Plant Physiol. 145: 1155-1160). The *Agrobacterium tumefaciens* host strain employed with the superbinary system is LBA4404(pSBI). Strain LBA4404(pSBI) harbors two independently-replicating plasmids, pAL4404 and pSBI. pAL4404 is a Ti-plasmid-derived helper plasmid which contains an intact set of vir genes (from Ti plasmid pTiACH5), but which has no T-DNA region (and thus no T-DNA left and right border repeat sequences). Plasmid pSBI supplies an additional partial set of vir genes derived from pTiBo542; this partial vir gene set includes the virB operon and the virC operon, as well as genes virG and virDI. One example of a shuttle vector used in the superbinary system is pSBI I, which contains a cloning polylinker that serves as an introduction site for genes destined for plant cell transformation, flanked by right and left T-DNA border repeat regions. Shuttle vector pSBI 1 is not capable of independent replication in *Agrobacterium*, but is stably maintained as a co-integrant plasmid when integrated into pSBI by means of homologous recombination between common sequences present on pSBI and pSBI I. Thus, the fully modified T-DNA region introduced into LBA4404 (pSBI) on a modified pSBI I vector is productively acted upon and transferred into plant cells by Vir proteins derived from two different *Agrobacterium* Ti plasmid sources (pTiACH5 and pTiBo542). The superbinary system has proven to be particularly useful in transformation of monocot plant species. See Hiei et al, (1994) Plant J. (6:271-282 and Ishida et al, (1996) Nat. Biotechnol. 14:745-750.

It will be clear that the dual T-DNA vector of the invention can also be prepared by conventional cloning techniques, as described herein after, instead of via the above described binary homologous recombination system.

Transformation of plant cells using *Agrobacterium* or any other bacteria can occur via protoplast co-cultivation, explant inoculation, floral dipping and vacuum infiltration. Such technologies are described, for example, in U.S. Pat. Nos. 5,177,010, 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, and 5,159,135. The use of T-DNA-containing vectors for the transformation of plant cells has been intensively researched and sufficiently described in European Patent Application 120516; An et al, (1985, EMBO J. 4:277-284), Fraley et al, (1986, Crit. Rev. Plant Sci. 4: 1-46), and Lee and Gelvin (2008, Plant Physiol. 146: 325-332).

Various tissue explants that can be transformed according to the invention include explants from hypocotyl, cotyledon, immature zygotic embryos, leaves, anthers, petals, ovules, roots, and meristems, stem cells and petioles. Also callus tissue can be transformed according to the invention. The term "callus", as used herein, refers to a disorganized mass of mainly embryogenic cells and cell clusters produced as a consequence of plant tissue culture. Friable callus refers to callus with a friable texture with the potential to form shoots and roots and eventually regenerate into whole plants. Compact callus can also have the potential to form shoots and roots. Callus can be regenerated/induced from various tissue explants as mentioned above.

In one embodiment, the plant cell of which the genome is modified according to the invention is transformed via transformation of a (friable) embryogenic callus cell, i.e. the cell is a (friable) embryogenic callus cell (comprised within (friable) embryogenic callus), as described below.

In another embodiment, the plant cell of which the genome is modified according to the invention is transformed via hypocotyl transformation, i.e. the plant cell is a hypocotyl cell (comprised within a hypocotyl). It is believed that hypocotyl transformation results in more pure modified events (a lower percentage of chimeric events).

The capability of inducing a double stranded break at a preselected site opens up several potential applications, i.e. insertion, replacement or deletion of one or more nucleotides. In case a DNA of interest present in the repair DNA molecule is to be inserted into the preselected site, this can occur by either homologous recombination, or by the process of non-homologous end-joining. The double stranded break may also be used to induce the formation of small deletions or insertions at the preselected site, thereby potentially inactivating a gene or regulatory element comprising the nucleotide sequence of the preselected site. The double stranded break at or in the vicinity of the preselected site will also facilitate replacement of a DNA region in the vicinity of the site of double strand break induction for a DNA of interest using a repair DNA, e.g. as described in WO 06/105946, WO08/037436 or WO08/148559.

If the double stranded DNA break induction is accompanied by the introduction of a repair DNA molecule which is used as a template, the double stranded break repair can occur basically in three ways. The repair DNA can be integrated into the genomic DNA at the DSB site by non-homologous end joining at both ends, or if one or two flanking regions with homology to the up- and/or downstream regions of the preselected site (the homology regions) are present in the repair DNA, integration of the repair DNA can also occur (partly) through homologous recombination. As such, the double stranded break near the preselected site will also facilitate replacement of a DNA region in the vicinity of the break for a DNA region of interest e.g. as described in WO 06/105946, WO08/037436 or WO08/148559.

To insert a DNA of interest by homologous recombination at the preselected site, the repair DNA may comprise at least one flanking DNA region having a nucleotide sequence which is similar to the nucleotide sequence of the DNA region upstream or downstream of the preselected site. The foreign DNA may also comprise two flanking DNA regions, located on opposite ends of the molecule and which have sufficient homology to nucleotide sequence of the DNA region upstream and downstream of the preselected site respectively to allow recombination between said flanking regions and said upstream and downstream region. Homology regions in the repair T-DNA may further prevent incidental co-integration of the DSBI T-DNA.

As used herein "a flanking DNA region" is a DNA region in the repair DNA with a nucleotide sequence having homology (i.e. high sequence identity) to the DNA regions respectively upstream or downstream of the target DNA sequence or preselected site (the homology regions). This allows to better control the insertion of DNA of interest. Indeed, integration by homologous recombination will allow precise joining of the DNA of interest to the plant nuclear genome up to the nucleotide level. Preferably, the recognition site of the DSBI enzyme is then located between the two homology regions. To facilitate replacement/deletion, there may also be more than one DSBI enzyme recognition site.

To have sufficient homology for recombination, the flanking DNA regions of the repair DNA may vary in length, and should be at least about 10 nucleotides in length. However, the flanking region may be as long as is practically possible (e.g. up to about 100-150 kb such as complete bacterial artificial chromosomes (BACs). Preferably, the flanking region will be about 25 bp to about 2000 bp, e.g. about 50 bp, 100 bp, 200 bp, 500 bp, 1000 or 1500 bp. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the DSB. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site or the target DNA sequence to be exchanged.

Moreover, the flanking region(s) of the repair DNA do not need to have homology to the regions immediately flanking the recognition site of the DSBI enzyme, but may have homology to a DNA region of the nuclear genome further remote from that site. Insertion of the DNA of interest will then result in a removal of the target DNA between the preselected insertion site and the DNA regions of homology. In other words, the target DNA located between the homology regions (i.e. the genomic regions with homology to the flanking regions of the repair DNA) will be substituted for the DNA of interest located between the two flanking regions of the repair DNA. When the repair DNA consists of the two flanking regions only, i.e. lacking any intervening sequences (DNA of interest), this approach can be used to specifically delete the genomic region located between the two homology regions.

The DNA of interest to be inserted may also comprise a selectable or screenable marker, which may or may not be removed after insertion, e.g as described in WO 06/105946, WO08/037436 or WO08/148559, to facilitate the identification of potentially correctly targeted events. Likewise, also the T-DNA encoding the DSBI enzyme may comprise a selectable or screenable marker gene, which preferably is different from the marker gene in the DNA of interest, to allow for (negative or counter) selection after segregation.

"Selectable or screenable markers" as used herein have their usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucuronidase (GUS), R-locus genes, green fluorescent protein and the likes.

It will be clear that the methods according to the invention allow insertion of any DNA of interest including DNA comprising a nucleotide sequence with a particular nucleotide sequence signature e.g. for subsequent identification, or DNA comprising (inducible) enhancers or silencers, e.g. to modulate the expression of the existing elite event. The DNA of interest may also comprise one or more plant expressible gene(s) of interest including but not limited to a herbicide tolerance gene, an insect resistance gene, a disease resistance gene, an abiotic stress resistance gene, an enzyme involved in oil biosynthesis or carbohydrate biosynthesis, an enzyme involved in fiber strength and/or length, an enzyme involved in the biosynthesis of secondary metabolites.

Herbicide-tolerance genes include a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a *Petunia* EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide tolerance genes may encode an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Herbicide-tolerance genes may also confer tolerance to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide tolerance genes encode variant ALS enzymes (also known as acetohydroxyacid synthase, AHAS) as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerance genes are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerance genes are described in for example WO 07/024782 and U.S. Patent Application No. 61/288,958.

Insect resistance gene may comprise a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at:

http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5);

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

An "insect-resistant gene as used herein, further includes transgenes comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Abiotic stress tolerance genes include 1) a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) a transgene capable of reducing the expression and/or the activity of the PARG encoding genes of the plants or plants cells, as described e.g. in WO 2004/090140.

3) a transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alteman, as disclosed in e.g. WO 00/47727, WO 00/73422, EP 06077301.7, U.S. Pat.

No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

It is also an embodiment of the invention to provide the combination of the T-DNA comprising the repair DNA and the T-DNA comprising the DSBI enzyme encoding gene, as well as a dual T-DNA vector (Ti or Ri plasmid) comprising those two DNAs and to provide *Agrobacterium* cells and strains comprising the combination of T-DNAs or comprising the dual T-DNA vector as described in the above methods. Plants or plant cells comprising the above T-DNA combination are also encompassed within the invention.

It will be appreciated that the methods of the invention can be applied to any plant (Angiospermae or Gymnospermae) including but not limited to cotton, canola, oilseed rape, soybean, vegetables, potatoes, *Lemna* spp., *Nicotiana* spp., *Arabidopsis*, alfalfa, barley, bean, corn, cotton, flax, millet, pea, rape, rice, rye, safflower, sorghum, soybean, sunflower, tobacco, turfgrass, wheat, asparagus, beet and sugar beet, broccoli, cabbage, carrot, cauliflower, celery, cucumber, eggplant, lettuce, onion, oilseed rape, pepper, potato, pumpkin, radish, spinach, squash, sugar cane, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells, plant parts and plants generated according to the methods of the invention, such as fruits, seeds, embryos, reproductive tissue, meristematic regions, callus tissue, leaves, roots, shoots, flowers, fibers, vascular tissue, gametophytes, sporophytes, pollen and microspores, which are characterised in that they comprise a specific modification in the genome (insertion, replacement and/or deletion). Gametes, seeds, embryos, either zygotic or somatic, progeny or hybrids of plants comprising the DNA modification events, which are produced by traditional breeding methods, are also included within the scope of the present invention. Such plants may contain a DNA of interest inserted at or instead of a target sequence or may have a specific DNA sequence deleted (even single nucleotides), and will only be different from their progenitor plants by the presence of this heterologous DNA or DNA sequence or the absence of the specifically deleted sequence (i.e. the intended modification) post exchange.

In some embodiments, the plant cells of the invention, i.e. a plant cell comprising the T-DNA combination as well as plant cells generated according to the methods of the invention comprising the intended genomic modification, may be a non-propagating cell, or a plant cell that cannot be regenerated into a plant, or a plant cell that cannot maintain its life by synthesizing carbohydrate and protein from the inorganics, such as water, carbon dioxide, and inorganic salt, through photosynthesis.

The plants obtained by the methods described herein may be further crossed by traditional breeding techniques with other plants to obtain progeny plants comprising the targeted DNA insertion events obtained according to the present invention. In this way, also the DSBI enzyme encoding T-DNA can be segregated out.

The invention further provides a method for producing a plant comprising a modification at a predefined site of the genome, comprising the step of crossing a plant generated according to the above methods with another plant or with itself and optionally harvesting seeds.

The invention further provides a method for producing feed, food or fiber comprising the steps of providing a population of plants generated according to the above methods and harvesting seeds.

The invention further provides a method for producing a cotton seed or a cotton fiber, comprising growing a cotton plant according to the above methods and isolating said seed or said fiber from said plant.

The plants and seeds according to the invention may be further treated with a chemical compound, e.g. if having tolerance such a chemical.

Accordingly, the invention also provides a method of growing a plant generated according to the above methods, comprising the step of applying a chemical to said plant or substrate wherein said plant is grown.

Further provided is a process of growing a plant in the field comprising the step of applying a chemical compound on a plant generated according to the above methods.

Also provided is a process of producing treated seed comprising the step applying a chemical compound, such as the chemicals described above, on a seed of plant generated according to the above described methods.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined may comprise additional DNA regions etc.

As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

A nucleic acid or nucleotide, as used herein, refers to both DNA and RNA. DNA also includes cDNA and genomic DNA. A nucleic acid molecules can be single- or double-stranded, and can be synthesized chemically or produced by biological expression in vitro or even in vivo.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The following non-limiting Examples describe the construction of a dual T-DNA vector comprising a DSBI enzyme encoding T-DNA and a repair DNA containing T-DNA as well as their use to efficiently produce plants with a targeted genomic modification.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications and publications mentioned herein are hereby incorporated by reference, in their entireties, for all purposes.

The sequence listing contained in the file named "BCS12-2004-WO1_ST25", which is 54 kilobytes (size as measured in Microsoft Windows®), contains 11 sequences SEQ ID NO: 1 through SEQ ID NO: 11, is filed herewith by electronic submission and is incorporated by reference herein.

The invention will be further described with reference to the examples described herein; however, it is to be understood that the invention is not limited to such examples.

SEQUENCE LISTING

Throughout the description and Examples, reference is made to the following sequences:

SEQ ID NO. 1: Nucleotide sequence of dual T-DNA vector pCTV231

SEQ ID NO. 2: Nucleotide sequence of dual T-DNA vector pTCV237

SEQ ID NO. 3: COT5/6 recognition sequence

SEQ ID NO. 4: Cotton genomic sequence comprising the COT5/6 recognition site

SEQ ID NO. 5: PCR primer IB527

SEQ ID NO. 6: PCR primer IB616

SEQ ID NO. 7: PCR primer IB589

SEQ ID NO. 8: PCR primer VDS382

SEQ ID NO. 9: PCR primer IB588

SEQ ID NO. 10: PCR primer IB303

SEQ ID NO. 11: PCR primer IB624

EXAMPLES

Example 1

Vector Construction

Using standard molecular biology techniques, the dual T-DNA vector pCV231 (SEQ ID NO. 1) was created, comprising between T-DNA borders the repair DNA comprising a 2mEPSPS and a Pf-HPPD-W336, and the meganuclease COT-5/6 gene between another pair of T-DNA borders (FIG. 1*a*):

Repair T-DNA:

- RB (nt 189 to 222): right border repeat from the T-DNA of *Agrobacterium tumefaciens* (Zambryski, 1988).
- 3'histonAt (nt 928 to 262): sequence including the 3' untranslated region of the histone H4 gene of *Arabidopsis thaliana* (Chabouté et al., 1987).
- hppdPfW336-1 Pa (nt 2021 to 945): coding sequence of the 4-hydroxyphenylpyruvate dioxygenase gene of *Pseudomonas fluorescens* strain A32 modified by the replacement of the amino acid Glycine 336 with a Tryptophane (Boudec et al., 1999), adapted to cotton codon usage.
- TPotpY-1 Pa (nt 2393 to 2024): coding sequence of an optimized transit peptide derivative (position 55 changed into Tyr), containing sequence of the RuBisCO small subunit genes of *Zea mays* (corn) and *Helianthus annuus* (sunflower) (Lebrun et al., 1996), adapted for cotton codon usage.
- PCsVMV XYZ (2914 to 2402): sequence including the promoter region of the Cassava Vein Mosaic Virus (Verdaguer et al., 1996).
- Ph4a748 (nt 3013-3929): sequence including the promoter region of the histone H4 gene of *Arabidopsis thaliana* (Chabouté et al., 1987).
- intron1 h3At (nt 3969 to 4434): first intron of gene II of the histone H3.III variant of *Arabidopsis thaliana* (Chaubet et al., 1992).
- TPotpC (nt 4448 to 4819): coding sequence of the optimized transit peptide, containing sequence of the RuBisCO small subunit genes of *Zea mays* (corn) and *Helianthus annuus* (sunflower) (Lebrun et al., 1996).
- 2mepsps (nt 4820 to 6157): coding sequence of the double-mutant 5-enol-pyruvylshikimate-3-phosphate synthase gene of *Zea mays* (corn) (Lebrun et al., 1997).
- 3'histonAt (nt 6178 to 6844): sequence including the 3' untranslated region of the histone H4 gene of *Arabidopsis thaliana* (Chabouté et al., 1987).
- LB (nt 6929 to 6952): left border repeat from the T-DNA of *Agrobacterium tumefaciens* (Zambryski, 1988).

COT5/6 meganuclease T-DNA:

- LB (nt 9211-9188): left border repeat from the T-DNA of *Agrobacterium tumefaciens* (Zambryski, 1988).
- P35S2c(fragment) (9236 to 9594): The P35S2c (fragment) is 123 bp shorter than P35S2c.
- P35S2c (nt 9236-10078): Sequence including the promoter region from the Cauliflower Mosaic Virus 35S transcript.
- COT-5/6-SC (nt 10085 to 11167): single-chain custom-made meganuclease from Precision BioScience which recognize the COT-5/6 recognition site 5' TAAAATTATTTACAAGTGTTTA.
- 3'nos (nt 11168 to 11427): sequence including the 3' untranslated region of the nopaline synthase gene from the T-DNA of pTiT37 (Depicker et al., 1982).
- RB (nt 11517-11493): right border repeat from the T-DNA of *Agrobacterium tumefaciens* (Zambryski, 1988).

This pTCV231 vector was used to transform *Agrobacterium* strain A5891 (=C58C1Rif(pTiEHA101).

Example 2

Cotton Transformation Using *Agrobacterium*

Friable cotton embryogenic callus (EC) of the target line containing in its nuclear genome the COT5/6 target sequence 5' TAAAATTATTTACAAGTGTTTA (SEQ ID NO. 3) was collected on 100 substrate and immersed for 20' in *Agrobacterium* suspension of $5\times10^8$ cells/ml in M100 substrate pH 5.2, with 100 μM acetosyringone (AS).

After 3 days co-cultivation in the dark at 24° C. on M100 with ½ concentration MS salts pH 5.2, with 100 μM AS and 100 mg/L L-cysteine, the EC is transferred as small piles on M100 substrate pH5.8, 250 mg/L triacillin and 1 mM glyphosate as selective agent and incubated in dim light at 28° C.

Example 3

Identification of Targeted Insertion Events

Glyphosate resistant calli were selected after a few subcultures on this substrate (M100 pH5.8 with 125 or 250 mg/L triacillin and 1 mM glyphosate). On the 575 glyphosate resistant calli thus obtained, a high throughput PCR screen was performed using the Expand High Fidelity PCR System (Roche) to identify candidate stacked events (see FIG. 1), resulting in the identification of 8 putative targeted insertion events (~1.4%), i.e. events where the repair DNA had been integrated into the target COT5/6 recognition site (table 1).

TABLE 1

Overview of PCR analysis on calli of putative targeted insertion events indicating amplicon length (bp) obtained per primer pair (theroretical length indicated between brackets, nd = not determined, — = no product obtained, *= weak product). See FIG. 1a for a schematic representation of the location of the primers and the theoretical amplicon length.

| Sample | IB527 × IB616 (2292) | IB527 × IB589 (3321) | IB527 × VDS382 (3387) | IB527 × IB588 (5455) | IB527 × IB303 (50011) | IB616 × VDS382 (2614) | IB616 × IB589 (1958) | Orientation |
|---|---|---|---|---|---|---|---|---|
| 74 | 2992 | ~3000 | nd | 5300 | nd | 2000/2500 | nd | + |
| 13 | 2992 | ~3000 | — | 5300 | nd | 2500 | nd | + |
| 33 | 2992 | ~4000 | — | 6300 | nd | — | nd | + |
| 23 | 2992 | ~3000 | — | 5300 | nd | 3500 | nd | + |
| 52 | 2992 | — | ~4000* | nd | 6000 | 5000 | nd | − |
| 75 | 2992 | — | ~3000* | nd | 4000 | nd | 2000 | − |
| 38 | — | ~3500 | ~4000* | 6000 | nd | — | nd | + |
| 66 | — | — | ~5000* | nd | 6500 | nd | ~2500 | − |

Next, sequence analysis was done on the candidate targeted insertion events to confirm that they were indeed stacked events (see FIG. 2). Although some variation exists in the transition between target plant genome and the insert due to the fact that the repair T-DNA lacks homology regions that can direct precise integration by homologous recombination, it was clear from the sequence data that in each of the analysed events the repair DNA had indeed been inserted into the COT5/6 recognition site. This occurred mostly without co-integration of the COT5/6 T-DNA, as the obtained lengths of the PCR products largely correspond to the theoretically expected lengths based on precise integration of the T-DNA into the COT5/6 recognition site (a much larger fragment could be indicative of incidental co-integration of the COT5/6 T-DNA).

Calli of targeted insertion events are grown into plants and will be further crossed to evaluate segregation of the COT5/6 gene.

When a similar experiment was performed using particle bombardment for co-delivery of the repair DNA and meganuclease encoding gene as described above (but wherein the repair DNA additionally contained homology regions for insertion via homologous recombination), 2065 glyphosate resistant events were obtained, of which 31 were found to be correctly targeted insertion events (~1.5%). Thus, using the dual T-DNA vector, the frequency of targeted insertions can be improved to a similar efficiency as can be obtained using direct DNA transfer methods.

Example 4

Double Stranded DNA Break Repair in the Presence of Sequence Homology

A similar vector as above but wherein the repair T-DNA additionally comprises flanking regions on one or both sides of the DNA region to be inserted (i.e. flanking the HPPD and 2mEPSPS gene cluster but within the T-DNA borders) which have homology to regions upstream and/or downstream of the preselected site respectively was constructed (pTCV237, represented by SEQ ID NO 2) comprising the following operably linked fragments:

Repair T-DNA:

RB (nt 189 to 222): right border repeat from the T-DNA of *Agrobacterium tumefaciens* (Zambryski, 1988).

FGD COT5/6 ds (nt 1804 to 254): 3' flanking region corresponding to genomic DNA downstream of the COT5/6 recognition site.

3'histonAt (nt 2547 to 1887): sequence including the 3' untranslated region of the histone H4 gene of *Arabidopsis thaliana* (Chabouté et al., 1987).

2mepsps (nt 3908 to 2571): coding sequence of the double-mutant 5-enol-pyruvylshikimate-3-phosphate synthase gene of *Zea mays* (corn) (Lebrun et al., 1997).

TPotpC (nt 4280 to 3909): coding sequence of the optimized transit peptide, containing sequence of the RuBisCO small subunit genes of *Zea mays* (corn) and *Helianthus annuus* (sunflower) (Lebrun et al., 1996).

intron1 h3At (nt 4749 to 4287): first intron of gene II of the histone H3.III variant of *Arabidopsis thaliana* (Chaubet et al., 1992).

Ph4a748 (nt 5715 to 4799): sequence including the promoter region of the histone H4 gene of *Arabidopsis thaliana* (Chabouté et al., 1987).

3'histonAt (nt 6459 to 5799): sequence including the 3' untranslated region of the histone H4 gene of *Arabidopsis thaliana* (Chabouté et al., 1987).

hppdPfW336-1 Pa (nt 7561 to 6485): coding sequence of the 4-hydroxyphenylpyruvate dioxygenase gene of *Pseudomonas fluorescens* strain A32 modified by the replacement of the amino acid Glycine 336 with a Tryptophane (Boudec et al., 1999), adapted to cotton codon usage.

TPotpY-1 Pa (nt 7933 to 7562): coding sequence of an optimized transit peptide derivative (position 55 changed into Tyr), containing sequence of the RuBisCO small subunit genes of *Zea mays* (corn) and *Helianthus annuus* (sunflower) (Lebrun et al., 1996), adapted for cotton codon usage.

5'cab22L (nt 8003 to 7935): Sequence including the leader sequence of the chlorophyll a/b binding protein gene of *Petunia hybrida* (Harpster et al., 1988).

P35S2 (nt 8421 to 8004): P35S2 promoter sequence.

FGD upstream COT5/6 us (nt 10523 to 8465): 5' flanking region corresponding to genomic DNA downstream of the COT5/6 recognition site.

LB (nt 10550 to 10573): left border repeat from the T-DNA of *Agrobacterium tumefaciens* (Zambryski, 1988).

COT5/6 meganuclease T-DNA:

LB (nt 12832 to 12809): left border repeat from the T-DNA of *Agrobacterium tumefaciens* (Zambryski, 1988).

P35S2c(fragment) (12857 to 13215): The P35S2c (fragment) is 123 bp shorter than P35S2c.

P35S2c (nt 13218 to 13699): Sequence including the promoter region from the Cauliflower Mosaic Virus 35S transcript.

COT-5/6-SC (nt 13706 to 14788): single-chain custom-made meganuclease from Precision BioScience which recognize the COT-5/6 recognition site 5"-TAAAATTATTTACAAGTGTTTA-3' (SEQ ID NO. 3).

3'nos (nt 14789 to 15048): sequence including the 3' untranslated region of the nopaline synthase gene from the T-DNA of pTiT37 (Depicker et al., 1982).

RB (nt 15138 to 15114): right border repeat from the T-DNA of *Agrobacterium tumefaciens* (Zambryski, 1988).

This vector was transformed into *Agrobacterium* and the resulting *Agrobacterium* strain was subsequently used to transform cotton cells from the target line, which were further cultured and selected as described above. Out of the glyphosate resistant calli, stacked events were identified by PCR and sequence analysis as described above (see also FIG. 1*b*).

On the 1167 glyphosate resistant calli thus obtained, a high throughput PCR screen was performed using the Expand High Fidelity PCR System (Roche) to identify candidate stacked events (see FIG. 1 *b*), resulting in the identification of a total 70 putative targeted insertion events (~6.0%), i.e. events where the repair DNA had been integrated into the target COT5/6 recognition site (table 1), as determined by PCR with primer pair 18527×18624 (resulting in a product of 2679 bp). An additional PCR product of 2992 bp with primer pair IB527×IB616 is indicative of the presence of also the non-modified target (i.e. a chimeric event), whereas the absence thereof is indicative for a pure stacked event (see Table 2).

TABLE 2

Overview of PCR analysis on calli of putative targeted insertion events obtained per primer pair (theoretical length indicated between brackets). See FIG. 1b for a schematic representation of the location of the primers and the theoretical amplicon length.

| No. of events | IB527 × IB624 (2679 bp) | IB527 × IB616 (2992 bp) |
|---|---|---|
| 64 | + | + |
| 6 | + | − |

The invention claimed is:

1. A method for modifying the nuclear genome of a cotton plant cell at a preselected site, comprising the steps of:

a. contacting a cotton plant cell with a bacterium capable of directing the transfer of T-DNA molecules from said bacterium into the nuclear genome of said plant cell, said bacterium comprising
   i. a first T-DNA molecule comprising between a first pair of T-DNA borders a chimeric gene encoding a plant-functional double stranded DNA break inducing (DSBI) enzyme, said DSBI enzyme being capable of recognizing and inducing a double stranded DNA break at a recognition site located at or within 1 kb of said preselected site, said chimeric gene comprising the following operably linked elements:
      1. A plant expressible promoter;
      2. a DNA region encoding a DSBI enzyme;
      3. a plant-functional 3' termination and polyadenylation region; and
   ii. a second T-DNA molecule comprising between a second pair of T-DNA borders a repair DNA molecule for use as a template for repair of said double stranded DNA break, wherein said repair DNA molecule comprises one or two flanking nucleotide sequences flanking the DNA molecule of interest, said flanking nucleotide sequence or sequences having at least 80% sequence identity over at least 50 nucleotides of the genomic DNA upstream and/or downstream of said preselected site to allow homologous recombination with said upstream and/or downstream DNA region, wherein said two T-DNA molecules are comprised within the same vector,
b. selecting a cotton plant cell wherein said repair DNA has been used as a template for repair of the double stranded DNA break, said repair of said double stranded DNA break resulting in a modification of said nuclear genome at said preselected site, wherein said modification is selected from
   i. a replacement of at least one nucleotide;
   ii. a deletion of at least one nucleotide;
   iii. an insertion of at least one nucleotide; or
   iv. any combination of i.-iii wherein said bacterium is an *Agrobacterium* spp.

wherein frequency of correctly targeted genome modification is increased compared to when two T-DNA molecules are in different vectors.

2. The method of claim 1, wherein said bacterium is *Agrobacterium tumefaciens.*

3. The method of claim 1, wherein said DSBI enzyme is non-naturally occurring.

4. The method of claim 1, wherein said repair DNA molecule comprises a DNA molecule of interest.

5. The method of claim 4, wherein said DNA molecule of interest comprises one or more plant expressible gene(s) of interest.

6. The method of claim 1, wherein said repair DNA molecule consists of two flanking nucleotide sequences, one of said flanking nucleotide sequence having at least 80% sequence identity over at least 50 nucleotides of the DNA region upstream of said predefined site, the other flanking nucleotide sequence having at least 80% sequence identity over at least 50 nucleotides of the DNA region downstream of said predefined site to allow homologous recombination between said flanking nucleotide sequences and said upstream and downstream DNA regions.

7. The method of claim 1, comprising the further step of growing said selected cotton plant cell into a cotton plant.

8. The method of claim 1, wherein said DSBI enzyme encoding gene and said modification genetically segregate in progeny of a cotton plant regenerated from said selected cotton plant cell.

9. A DNA vector comprising a first and a second T-DNA molecule as described in claim 1.

10. A bacterium capable of directing the transfer of T-DNA molecules from said bacterium into the nuclear genome of a cotton plant cell, said bacterium comprising the first and second T-DNA molecules as described in claim 1 or the DNA vector as described in claim 9, wherein said bacterium is an *Agrobacterium* spp.

11. The bacterium of claim 10, which is *Agrobacterium tumefaciens.*

12. The method of claim 5, wherein said plant expressible gene of interest is an herbicide tolerance gene, a gene encoding an enzyme involved in oil biosynthesis—or carbohydrate biosynthesis, a gene encoding an enzyme involved in fiber strength or fiber length, a gene encoding an enzyme involved in biosynthesis of secondary metabolites, insect resistance gene, a disease resistance gene, or an abiotic stress resistance gene.

13. A method for modifying the nuclear genome of a plant cell at a preselected site, comprising the steps of:

a. contacting a plant cell with a bacterium capable of directing the transfer of T-DNA molecules from said bacterium into the nuclear genome of said plant cell, said bacterium comprising
   i. a first T-DNA molecule comprising between a first pair of T-DNA borders a chimeric gene encoding a plant-functional double stranded DNA break inducing (DSBI) enzyme, said DSBI enzyme being capable of recognizing and inducing a double stranded DNA break at a recognition site located at or within 1 kb of said preselected site, said chimeric gene comprising the following operably linked elements:

1. A plant expressible promoter;
2. a DNA region encoding a DSBI enzyme;
3. a plant-functional 3' termination and polyadenylation region; and ii. a second T-DNA molecule comprising between a second pair of T-DNA borders a repair DNA molecule for use as a template for repair of said double stranded DNA break, wherein said repair DNA molecule comprises one or two flanking nucleotide sequences flanking the DNA molecule of interest, said flanking nucleotide sequence or sequences having at least 80% sequence identity over at least 50 nucleotides of the genomic DNA upstream and/or downstream of said preselected site to allow homologous recombination with said upstream and/or downstream DNA region, wherein said two T-DNA molecules are comprised within the same vector, b. selecting a plant cell wherein said repair DNA has been used as a template for repair of the double stranded DNA break, said repair of said double stranded DNA break resulting in a modification of said nuclear genome at said preselected site, wherein said modification is selected from i. a replacement of at least one nucleotide;
ii. a deletion of at least one nucleotide;
iii. an insertion of at least one nucleotide; or
iv. any combination of i.-iii wherein said bacterium is an *Agrobacterium* spp.

wherein frequency of correctly targeted genome modification is increased compared to when two T-DNA molecules are in different vectors.

* * * * *

SEQUENCE LISTING

```
<160> NUMBER OF SEQ ID NOS: 19

<210> SEQ ID NO 1
<211> LENGTH: 16697
<212> TYPE: DNA
<213> ORGANISM: Artificial Sequence
<220> FEATURE:
<223> OTHER INFORMATION: vector

<400> SEQUENCE: 1

agattcgaag ctcggtcccg tgggtgttct gtcgtctcgt tgtacaacga aatccattcc      60

cattccgcgc tcaagatggc ttcccctcgg cagttcatca gggctaaatc aatctagccg     120

acttgtccgg tgaaatgggc tgcactccaa cagaaacaat caaacaaaca tacacagcga     180

cttattcaca cgcgacaaat tacaacggta tatatcctgc cagtactcgg ccgtcgacct     240

gcaggcccgg gttaattaag gcccgatcaa atctgaggga cgttaaagcg atgataaatt     300

ggaaccagaa tatagaatct ttgttctgct ctagcttttc ttctgtacat tttttacgat     360
```

```
tagactatga ttttcattca ataaccaaaa ttctgaagtt tgtcatcaag ttgctcaatc    420
aaacttgtac cggtttgttt cggttttata tcagctcact gttacacttt aaccaaaatc    480
ggtttatgtc ttaataaagg aattgagtcg gtttaactca tatccgtacc aatgcgacgt    540
cgtgtccgcg tttcagtagc tttgctcatt gtcttctacg ggaactttcc cggacatagg    600
aaccgccctt tcgttatcct catccatcgt gaaatcagga aataaatgtt cgaagatttg    660
aggtcaaaag tcgaatttca tgttgtctct tctatttaga tacaaaattg aagcaatttt    720
caccaattta atgccaaaat ttaaaacaac gctgataaag tgaaacttga ttcgatttat    780
atttcaaccg aaactgctga agcaagaaga aaaagcgtaa ttacacataa caagaacgct    840
accgcaaact actaaacgcc aaacccaata caaaagtaaa acgcagacgc ttaagtgaga    900
aacccagaaa acacaaacgc ggatcgggcg acgcgtgcta gcttttaatc agcggtcaaa    960
acccctctac gaacttgatc cctctctatc gattcgaaaa gtgctttgaa gttccattct   1020
ccgaagccat cgtccccttt acgctgaatg aactcaaaga aaacgggtcc catgagagtc   1080
tcggaaaaga tttgtaacag gagcctctta tcaccctcaa ccgaagaacc atcgagaagt   1140
ataccccctgg cttgcagttg gtccacgggt tccccatgat caggcaggcg tccttctagc   1200
atctcatagt aagtatcggg aggtgcagtc atgaatctca tacctatctt cttcaatgca   1260
tcccaggttt tcacaagatc atcagtcaga aaagcgacat gctgaatgcc ttcaccattg   1320
aactgcataa gaaactcttc gatttgtcct gcacctttgc ttgactcttc gttgagtgga   1380
atccttatca taccatctgg agcgctcata gcctttgatg tgagaccagt atactctcct   1440
ttgatgtcaa agtatctagc ttccctaaag ttgaagagtt tctcatagaa gttagcccag   1500
tataccattc gtccacgata gacgttgtgt gtcaaatgat caataacctt caagccagca   1560
ccgacaggat ttcgttccac gccttcaaga tagacgaaat ctatgtcgta gatagaactg   1620
ccctctccga atctgtcgat aagatacaac ggtgcaccac cgatgccttt gatggctgga   1680
agattcaatt ccataggtcc agtgtcaatg tgaataggct gagctccaag ttctaatgcc   1740
ctattgtagg ctttctggga atccttaact cgaaatgcca tgccacaaac ggatggtcca   1800
tgttcggcag caaagtagct tgctatagag ttaggttcgt tgttcaagat caggttaatc   1860
tctccttgcc gatataggtg cacgttctta ctgcgatgtg tagctacctt agtaaacccc   1920
ataatctcaa agatgggttc aagggtccca ggtgtaggag aagcaaactc aatgaactcg   1980
aaacccatga gtcccatagg attctcgtat agatcagcca tgcatctaat cctacctccg   2040
ttgctaacat tccccagcga tctggaagat ctccgagcaa ctggcaaact agcagtactc   2100
ttcaaccctt gaaatggtgc cacagctgtg gcagagctgg ccatcatcac agtgggagcc   2160
atagatagcg gaggtaagta ggataaggtc tcaaacttct tgttgccata ggctggccag   2220
acttgcatat actgtactct cccaccgttg ctcggaagtg ttgagaagtc attagccttc   2280
ttagtggttg gaaatgcagc atttgactta agacctgtga acggagccac catattagct   2340
tgggctggtg cggtacgtga aacagtggca actgaagatg aaatactagc catggttttg   2400
gacaaactta caaatttctc tgaagttgta tcctcagtac ttcaaagaaa atagcttaca   2460
ccaaattttt tcttgttttc acaaatgccg aacttggttc cttatatagg aaaactcaag   2520
ggcaaaaatg acacggaaaa atataaaagg ataagtagtg gggataaaga ttcctttgtg   2580
ataaggttac tttccgccct tacattttcc accttacatg tgtcctctat gtctctttca   2640
caatcaccga ccttatcttc ttcttttcat tgttgtcgtc agtgcttacg tcttcaagat   2700
tcttttcttc gcctggttct tctttttcaa tttctacgta ttcttcttcg tattctggca   2760
```

```
gtataggatc ttgtatctgt acattcttca tttttgaaca taggttgcat atgtgccgca   2820
tattgatctg cttcttgctg agctcacata atacttccat agtttttccc gtaaacattg   2880
gattcttgat gctacatctt ggataattac cttcgcggcc gcttggcgcg ccgaattcga   2940
tatcattacc ctgttatccc taaagcttat taatataact tcgtatagca tacattatac   3000
gaagttatgt ttgtcgagga gaaatatgag tcgaggcatg gatacactaa gttcccctga   3060
agtgagcatg atctttgatg ctgagatgat tcccagagca agatagtttg tgctgcaagt   3120
gacacaattg taatgaaacc accactcaac gaatttactt gtggctttga catgtcgtgt   3180
gctctgtttg tatttgtgag tgccggttgg taattatttt tgttaatgtg attttaaaac   3240
ctcttatgta aatagttact ttatctattg aagtgtgttc ttgtggtcta tagtttctca   3300
aagggaaatt aaaatgttga catcccattt acaattgata acttggtata cacaaacttt   3360
gtaaatttgg tgatatttat ggtcgaaaga aggcaatacc cattgtatgt tccaatatca   3420
atatcaatac gataacttga taatactaac atatgattgt cattgttttt ccagtatcaa   3480
tatacattaa gctactacaa aattagtata aatcactata ttataaatct tttcggttg   3540
taacttgtaa ttcgtgggtt tttaaaataa aagcatgtga aaattttcaa ataatgtgat   3600
ggcgcaattt tattttccga gttccaaaat attgccgctt cattacccta atttgtggcg   3660
ccacatgtaa aacaaaagac gattcttagt ggctatcact gccatcacgc ggatcactaa   3720
tatgaaccgt cgattaaaac agatcgacgg tttatacatc attttattgt acacacggat   3780
cgatatctca gccgttagat ttaatatgcg atctgattgc tcaaaaaata gactctccgt   3840
ctttgcctat aaaaacaatt tcacatcttt ctcacccaaa tctactctta accgttcttc   3900
ttcttctaca gacatcaatt tctctcgact ctagaggatc caagcttatc gatttcgaac   3960
ccctcaggcg aagaacaggt atgatttgtt tgtaattaga tcaggggttt aggtctttcc   4020
attacttttt aatgtttttt ctgttactgt ctccgcgatc tgattttacg acaatagagt   4080
ttcgggtttt gtcccattcc agtttgaaaa taaaggtccg tcttttaagt ttgctggatc   4140
gataaacctg tgaagattga gtctagtcga tttattggat gatccattct tcatcgtttt   4200
tttcttgctt cgaagttctg tataaccaga tttgtctgtg tgcgattgtc attacctagc   4260
cgtgtatcga gaactagggt tttcgagtca attttgcccc ttttggttat atctggttcg   4320
ataacgattc atctggatta gggttttaag tggtgacgtt tagtattcca atttcttcaa   4380
aatttagtta tggataatga aaatccccaa ttgactgttc aatttcttgt taaatgcgca   4440
gatcacaatg gcttcgatct cctcctcagt cgcgaccgtt agccggaccg cccctgctca   4500
ggccaacatg gtggctccgt tcaccggcct taagtccaac gccgccttcc ccaccaccaa   4560
gaaggctaac gacttctcca cccttcccag caacggtgga agagttcaat gtatgcaggt   4620
gtggccggcc tacggcaaca agaagttcga gacgctgtcg tacctgccgc cgctgtctat   4680
ggcgcccacc gtgatgatgg cctcgtcggc caccgccgtc gctccgttcc aggggctcaa   4740
gtccaccgcc agcctccccg tcgcccgccg ctcctccaga agcctcggca acgtcagcaa   4800
cggcggaagg atccggtgca tggccggcgc cgaggagatc gtgctgcagc ccatcaagga   4860
gatctccggc accgtcaagc tgccggggtc caagtcgctt tccaaccgga tcctcctact   4920
cgccgccctg tccgagggga caacagtggt tgataacctg ctgaacagtg aggatgtcca   4980
ctacatgctc ggggccttga ggactcttgg tctctctgtc gaagcggaca aagctgccaa   5040
aagagctgta gttgttggct gtggtggaaa gttcccagtt gaggatgcta aagaggaagt   5100
```

-continued

```
gcagctcttc ttggggaatg ctggaatcgc aatgcggtcc ttgacagcag ctgttactgc   5160
tgctggtgga aatgcaactt acgtgcttga tggagtacca agaatgaggg agagacccat   5220
tggcgacttg gttgtcggat tgaagcagct tggtgcagat gttgattgtt tccttggcac   5280
tgactgccca cctgttcgtg tcaatggaat cggagggcta cctggtggca aggtcaagct   5340
gtctggctcc atcagcagtc agtacttgag tgccttgctg atggctgctc ctttggctct   5400
tggggatgtg gagattgaaa tcattgataa attaatctcc attccgtacg tcgaaatgac   5460
attgagattg atggagcgtt ttggtgtgaa agcagagcat tctgatagct gggacagatt   5520
ctacattaag ggaggtcaaa aatacaagtc ccctaaaaat gcctatgttg aaggtgatgc   5580
ctcaagcgca agctatttct tggctggtgc tgcaattact ggagggactg tgactgtgga   5640
aggttgtggc accaccagtt tgcagggtga tgtgaagttt gctgaggtac tggagatgat   5700
gggagcgaag gttacatgga ccgagactag cgtaactgtt actggcccac cgcgggagcc   5760
atttgggagg aaacacctca aggcgattga tgtcaacatg aacaagatgc ctgatgtcgc   5820
catgactctt gctgtggttg ccctctttgc cgatggcccg acagccatca gagacgtggc   5880
ttcctggaga gtaaaggaga ccgagaggat ggttgcgatc cggacggagc taaccaagct   5940
gggagcatct gttgaggaag ggccggacta ctgcatcatc acgccgccgg agaagctgaa   6000
cgtgacggcg atcgacacgt acgacgacca caggatggcg atggctttct cccttgccgc   6060
ctgtgccgag gtccccgtca ccatccggga ccctgggtgc acccggaaga ccttccccga   6120
ctacttcgat gtgctgagca ctttcgtcaa gaattaagct ctagaactag tggatccccc   6180
gatccgcgtt tgtgttttct gggtttctca cttaagcgtc tgcgttttac ttttgtattg   6240
ggtttggcgt ttagtagttt gcggtagcgt tcttgttatg tgtaattacg ctttttcttc   6300
ttgcttcagc agtttcggtt gaaatataaa tcgaatcaag tttcacttta tcagcgttgt   6360
tttaaatttt ggcattaaat tggtgaaaat tgcttcaatt ttgtatctaa atagaagaga   6420
caacatgaaa ttcgactttt gacctcaaat cttcgaacat ttatttcctg atttcacgat   6480
ggatgaggat aacgaaaggg cggttcctat gtccgggaaa gttcccgtag aagacaatga   6540
gcaaagctac tgaaacgcgg acacgacgtc gcattggtac ggatatgagt taaaccgact   6600
caattccttt attaagacat aaaccgattt tggttaaagt gtaacagtga gctgatataa   6660
aaccgaaaca aaccggtaca agtttgattg agcaacttga tgacaaactt cagaattttg   6720
gttattgaat gaaaatcata gtctaatcgt aaaaaatgta cagaagaaaa gctagagcag   6780
aacaaagatt ctatattctg gttccaattt atcatcgctt taacgtccct cagatttgat   6840
cgggaaacat aacttcgtat agcatacatt atacgaagtt atcaaaacgt cgtgagacag   6900
tttggttgta gcgatcgcca tggagccatt tacaattgaa tatatcctgc cgccgctgcc   6960
gctttgcacc cggtggagct tgcatgttgg tttctacgca gaactgagcc ggttaggcag   7020
ataatttcca ttgagaactg agccatgtgc accttccccc caacacggtg agcgacgggg   7080
caacggagtg atccacatgg gacttttaaa catcatccgt cggatggcgt tgcgagagaa   7140
gcagtcgatc cgtgagatca gccgacgcac cgggcaggcg cgcaacacga tcgcaaagta   7200
tttgaacgca ggtacaatcg agccgacgtt cacggtaccg gaacgaccaa gcaagctagc   7260
ttagtaaagc cctcgctaga ttttaatgcg gatgttgcga ttacttcgcc aactattgcg   7320
ataacaagaa aaagccagcc tttcatgata tatctcccaa tttgtgtagg gcttattatg   7380
cacgcttaaa aataataaaa gcagacttga cctgatagtt tggctgtgag caattatgtg   7440
cttagtgcat ctaacgcttg agttaagccg cgccgcgaag cggcgtcggc ttgaacgaat   7500
```

```
tgttagacat tatttgccga ctaccttggt gatctcgcct ttcacgtagt ggacaaattc   7560
ttccaactga tctgcgcgcg aggccaagcg atcttcttct tgtccaagat aagcctgtct   7620
agcttcaagt atgacgggct gatactgggc cggcaggcgc tccattgccc agtcggcagc   7680
gacatccttc ggcgcgattt tgccggttac tgcgctgtac caaatgcggg acaacgtaag   7740
cactacattt cgctcatcgc cagcccagtc gggcggcgag ttccatagcg ttaaggtttc   7800
atttagcgcc tcaaatagat cctgttcagg aaccggatca aagagttcct ccgccgctgg   7860
acctaccaag gcaacgctat gttctcttgc ttttgtcagc aagatagcca gatcaatgtc   7920
gatcgtggct ggctcgaaga tacctgcaag aatgtcattg cgctgccatt ctccaaattg   7980
cagttcgcgc ttagctggat aacgccacgg aatgatgtcg tcgtgcacaa caatggtgac   8040
ttctacagcg cggagaatct cgctctctcc aggggaagcc gaagtttcca aaaggtcgtt   8100
gatcaaagct cgccgcgttg tttcatcaag ccttacggtc accgtaacca gcaaatcaat   8160
atcactgtgt ggcttcaggc cgccatccac tgcggagccg tacaaatgta cggccagcaa   8220
cgtcggttcg agatggcgct cgatgacgcc aactacctct gatagttgag tcgatacttc   8280
ggcgatcacc gcttccctca tgatgtttaa ctttgtttta gggcgactgc cctgctgcgt   8340
aacatcgttg ctgctccata acatcaaaca tcgacccacg gcgtaacgcg cttgctgctt   8400
ggatgcccga ggcatagact gtaccccaaa aaaacagtca taacaagcca tgaaaaccgc   8460
cactgcgccg ttaccaccgc tgcgttcggt caaggttctg gaccagttgc gtgagcgcat   8520
acgctacttg cattacagct tacgaaccga acaggcttat gtccactggg ttcgtgcctt   8580
catccgtttc cacggtgtgc gtcacccggc aaccttgggc agcagcgaag tcgaggcatt   8640
tctgtcctgg ctggcgaacg agcgcaaggt ttcggtctcc acgcatcgtc aggcattggc   8700
ggccttgctg ttcttctacg gcaaggtgct gtgcacggat ctgccctggc ttcaggagat   8760
cggaagacct cggccgtcgc ggcgcttgcc ggtggtgctg accccggatg aagtggttcg   8820
catcctcggt tttctggaag gcgagcatcg tttgttcgcc cagcttctgt atggaacggg   8880
catgcttgct tggtcgttcc ggtaccgtga acgtcggctc gattgtacct gcgttcaaat   8940
actttgcgat cgtgttgcgc gcctgcccgg tgcgtcggct gatctcacgg atcgactgct   9000
tctctcgcaa cgccatccga cggatgatgt ttaaaagtcc catgtggatc actccgttgc   9060
cccgtcgctc accgtgttgg ggggaaggtg cacatggctc agttctcaat ggaaattatc   9120
tgcctaaccg gctcagttct gcgtagaaac caacatgcaa gctccaccgg gtgcaaagcg   9180
gcagcggcgg caggatatat tcaattgtaa atggctccat gcgttaatta agcttgagag   9240
gcggtttgcg tattggctag agcagcttgc caacatggtg gagcacgaca ctctcgtcta   9300
ctccaagaat atcaaagata cagtctcaga agaccaaagg gctattgaga cttttcaaca   9360
aagggtaata tcgggaaacc tcctcggatt ccattgccca gctatctgtc acttcatcaa   9420
aaggacagta gaaaaggaag gtggcaccta caaatgccat cattgcgata aaggaaaggc   9480
tatcgttcaa gatgcctctg ccgacagtgg tcccaaagat ggacccccac ccacgaggag   9540
catcgtggaa aaagaagacg ttccaaccac gtcttcaaag caagtggatt gatgtgaaca   9600
tggtggagca cgacactctc gtctactcca agaatatcaa agatacagtc tcagaagacc   9660
aaagggctat tgagactttt caacaaaggg taatatcggg aaacctcctc ggattccatt   9720
gcccagctat ctgtcacttc atcaaaagga cagtagaaaa ggaaggtggc acctacaaat   9780
gccatcattg cgataaagga aaggctatcg ttcaagatgc ctctgccgac agtggtccca   9840
```

```
aagatggacc cccacccacg aggagcatcg tggaaaaaga agacgttcca accacgtctt   9900
caaagcaagt ggattgatgt gatatctcca ctgacgtaag ggatgacgca caatcccact   9960
atccttcgca agacccttcc tctatataag gaagttcatt tcatttggag aggacacgct  10020
gaaatcacca gtctctctct acaaatctat ctctctcgag ctttcgcaga tctgtcgaac  10080
caccatggca ccgaagaaga agcgcaaggt gcatatgaac accaagtaca acaaggagtt  10140
cctgctctac ctggcgggct tcgtggacgg ggacggctcc atcatcgccc agatcaagcc  10200
gaaccagtcc tacaagttca agcatcagct gtccctcacc ttcaccgtca cccagaagac  10260
acagcgccgt tggttcctcg acaagctggt ggacgagatc ggagtgggct acgtgtacga  10320
ccagggcagc gtctcccact accgcctgtc ccagatcaag cctctgcaca acttcctgac  10380
ccagctccag cccttcctga agctcaagca gaagcaggcc aacctcgtgc tgaagatcat  10440
cgagcagctg ccctccgcca aggaatcccc ggacaagttc ctggaggtgt gcacgtgggt  10500
ggaccagatc gcggccctca acgacagcaa gacccgcaag acgacctcgg agacggtgcg  10560
ggcggtcctg gactccctcc caggatccgt gggaggtcta tcgccatctc aggcatccag  10620
cgccgcatcc tcggcttcct caagcccggg ttcagggatc tccgaagcac tcagagctgg  10680
agcaactaag tccaaggaat tcctgctcta cctggcgggc ttcgtcgacg gggacggctc  10740
catcaaggcc gcgatcaagc cgaaccagtc ctacaagttc aagcatcagc tgtccctcac  10800
cttccaggtc acgcagaaga cacagcgccg ttggttcctc gacaagctgg tggacgagat  10860
cggggtgggc tacgtgtacg actccggcag cgtctccgac taccagctgt cccagatcaa  10920
gcctctgcac aacttcctga cccagctcca gcccttcctg aagctcaagc agaagcaggc  10980
caacctcgtg ctgaagatca tcgagcagct gccctccgcc aaggaatccc cggacaagtt  11040
cctggaggtg tgcacctggg tggaccagat cgccgctctg aacgactcca agacccgcaa  11100
gaccacttcc gagaccgtcc gcgccgttct agacagtctc tccgagaaga agaagtcgtc  11160
cccctagcat gccgttcaaa catttggcaa taaagtttct taagattgaa tcctgttgcc  11220
ggtcttgcga tgattatcat ataatttctg ttgaattacg ttaagcatgt aataattaac  11280
atgtaatgca tgacgttatt tatgagatgg gtttttatga ttagagtccc gcaattatac  11340
atttaatacg cgatagaaaa caaaatatag cgcgcaaact aggataaatt atcgcgcgcg  11400
gtgtcatcta tgttactaga tcgggcccac tagtcgaccg catgacttaa ttaagtcatg  11460
cggtcgacta gtgcaggtcg acggccgagt actggcagga tatataccgt tgtaatttgt  11520
cgcgtgtgaa taagtcgctg tgtatgtttg tttgattgtt tctgttggag tgcagcccat  11580
ttcaccggac aagtcggcta gattgattta gccctgatga actgccgagg ggaagccatc  11640
ttgagcgcgg aatgggaatg gatttcgttg tacaacgaga cgacagaaca cccacgggct  11700
ccaaggatcg ggccttgatg ttacccgaga gcttggcacc cagcctgcgc gagcaggatc  11760
gatccaaccc ctccgctgct atagtgcagt cggcttctga cgttcagtgc agccgtcttc  11820
tgaaaacgac atgtcgcaca agtcctaagt tacgcgacag gctgccgccc tgcccttttc  11880
ctggcgtttt cttgtcgcgt gttttagtcg cataaagtag aatacttgcg actagaaccg  11940
gagacattac gccatgaaca agagcgccgc cgctggcctg ctgggctatg cccgcgtcag  12000
caccgacgac caggacttga ccaaccaacg ggccgaactg cacgcggccg gctgcaccaa  12060
gctgttttcc gagaagatca ccggcaccag gcgcgaccgc ccggagctgg ccaggatgct  12120
tgaccaccta cgccctggcg acgttgtgac agtgaccagg ctagaccgcc tggcccgcag  12180
cacccgcgac ctactggaca ttgccgagcg catccaggag gccggcgcgg gcctgcgtag  12240
```

```
cctggcagag ccgtgggccg acaccaccac gccggccggc cgcatggtgt tgaccgtgtt  12300
cgccggcatt gccgagttcg agcgttccct aatcatcgac cgcacccgga gcgggcgcga  12360
ggccgccaag gcccgaggcg tgaagtttgg cccccgccct accctcaccc cggcacagat  12420
cgcgcacgcc cgcgagctga tcgaccagga aggccgcacc gtgaaagagg cggctgcact  12480
gcttggcgtg catcgctcga ccctgtaccg cgcacttgag cgcagcgagg aagtgacgcc  12540
caccgaggcc aggcggcgcg gtgccttccg tgaggacgca ttgaccgagg ccgacgccct  12600
ggcggccgcc gagaatgaac gccaagagga acaagcatga aaccgcacca ggacggccag  12660
gacgaaccgt ttttcattac cgaagagatc gaggcggaga tgatcgcggc cgggtacgtg  12720
ttcgagccgc ccgcgcacgt ctcaaccgtg cggctgcatg aaatcctggc cggtttgtct  12780
gatgccaagc tggcggcctg gccggccagc ttggccgctg aagaaaccga gcgccgccgt  12840
ctaaaaaggt gatgtgtatt tgagtaaaac agcttgcgtc atgcggtcgc tgcgtatatg  12900
atgcgatgag taaataaaca aatacgcaag gggaacgcat gaaggttatc gctgtactta  12960
accagaaagg cgggtcaggc aagacgacca tcgcaaccca tctagcccgc gccctgcaac  13020
tcgccggggc cgatgttctg ttagtcgatt ccgatcccca gggcagtgcc cgcgattggg  13080
cggccgtgcg ggaagatcaa ccgctaaccg ttgtcggcat cgaccgcccg acgattgacc  13140
gcgacgtgaa ggccatcggc cggcgcgact tcgtagtgat cgacggagcg ccccaggcgg  13200
cggacttggc tgtgtccgcg atcaaggcag ccgacttcgt gctgattccg gtgcagccaa  13260
gcccttacga catatgggcc accgccgacc tggtggagct ggttaagcag cgcattgagg  13320
tcacggatgg aaggctacaa gcggcctttg tcgtgtcgcg ggcgatcaaa ggcacgcgca  13380
tcggcggtga ggttgccgag gcgctggccg ggtacgagct gcccattctt gagtcccgta  13440
tcacgcagcg cgtgagctac ccaggcactg ccgccgccgg cacaaccgtt cttgaatcag  13500
aacccgaggg cgacgctgcc cgcgaggtcc aggcgctggc cgctgaaatt aaatcaaaac  13560
tcatttgagt taatgaggta aagagaaaat gagcaaaagc acaaacacgc taagtgccgg  13620
ccgtccgagc gcacgcagca gcaaggctgc aacgttggcc agcctggcag acacgccagc  13680
catgaagcgg gtcaactttc agttgccggc ggaggatcac accaagctga agatgtacgc  13740
ggtacgccaa ggcaagacca ttaccgagct gctatctgaa tacatcgcgc agctaccaga  13800
gtaaatgagc aaatgaataa atgagtagat gaattttagc ggctaaagga ggcggcatgg  13860
aaaatcaaga acaaccaggc accgacgccg tggaatgccc catgtgtgga ggaacgggcg  13920
gttggccagg cgtaagcggc tgggttgtct gccggccctg caatggcact ggaaccccca  13980
agcccgagga atcggcgtga cggtcgcaaa ccatccggcc cggtacaaat cggcgcggcg  14040
ctgggtgatg acctggtgga gaagttgaag gccgcgcagg ccgcccagcg gcaacgcatc  14100
gaggcagaag cacgccccgg tgaatcgtgg caagcggccg ctgatcgaat ccgcaaagaa  14160
tcccggcaac cgccggcagc cggtgcgccg tcgattagga agccgcccaa gggcgacgag  14220
caaccagatt ttttcgttcc gatgctctat gacgtgggca cccgcgatag tcgcagcatc  14280
atggacgtgg ccgttttccg tctgtcgaag cgtgaccgac gagctggcga ggtgatccgc  14340
tacgagcttc cagacgggca cgtagaggtt tccgcagggc cggccggcat ggccagtgtg  14400
tgggattacg acctggtact gatggcggtt tcccatctaa ccgaatccat gaaccgatac  14460
cgggaaggga agggagacaa gcccggccgc gtgttccgtc cacacgttgc ggacgtactc  14520
aagttctgcc ggcgagccga tggcggaaag cagaaagacg acctggtaga aacctgcatt  14580
```

```
cggttaaaca ccacgcacgt tgccatgcag cgtacgaaga aggccaagaa cggccgcctg  14640
gtgacggtat ccgagggtga agccttgatt agccgctaca agatcgtaaa gagcgaaacc  14700
gggcggccgg agtacatcga gatcgagcta gctgattgga tgtaccgcga gatcacagaa  14760
ggcaagaacc cggacgtgct gacggttcac cccgattact ttttgatcga tcccggcatc  14820
ggccgttttc tctaccgcct ggcacgccgc gccgcaggca aggcagaagc cagatggttg  14880
ttcaagacga tctacgaacg cagtggcagc gccggagagt tcaagaagtt ctgtttcacc  14940
gtgcgcaagc tgatcgggtc aaatgacctg ccggagtacg atttgaagga ggaggcgggg  15000
caggctggcc cgatcctagt catgcgctac cgcaacctga tcgagggcga agcatccgcc  15060
ggttcctaat gtacggagca gatgctaggg caaattgccc tagcagggga aaaaggtcga  15120
aaaggtctct ttcctgtgga tagcacgtac attgggaacc caaagccgta cattgggaac  15180
cggaacccgt acattgggaa cccaaagccg tacattggga accggtcaca catgtaagtg  15240
actgatataa aagagaaaaa aggcgatttt tccgcctaaa actctttaaa acttattaaa  15300
actcttaaaa cccgcctggc ctgtgcataa ctgtctggcc agcgcacagc cgaagagctg  15360
caaaaagcgc ctacccttcg gtcgctgcgc tccctacgcc ccgccgcttc gcgtcggcct  15420
atcgcggccg ctggccgctc aaaaatggct ggcctacggc caggcaatct accagggcgc  15480
ggacaagccg cgccgtcgcc actcgaccgc cggcgcccac atcaaggcac cctgcctcgc  15540
gcgtttcggt gatgacggtg aaaacctctg acacatgcag ctcccggaga cggtcacagc  15600
ttgtctgtaa gcggatgccg ggagcagaca agcccgtcag ggcgcgtcag cgggtgttgg  15660
cgggtgtcgg ggcgcagcca tgacccagtc acgtagcgat agcggagtgt atactggctt  15720
aactatgcgg catcagagca gattgtactg agagtgcacc atatgcggtg tgaaataccg  15780
cacagatgcg taaggagaaa ataccgcatc aggcgctctt ccgcttcctc gctcactgac  15840
tcgctgcgct cggtcgttcg gctgcggcga gcggtatcag ctcactcaaa ggcggtaata  15900
cggttatcca cagaatcagg ggataacgca ggaaagaaca tgtgagcaaa aggccagcaa  15960
aaggccagga accgtaaaaa ggccgcgttg ctggcgtttt tccataggct ccgcccccct  16020
gacgagcatc acaaaaatcg acgctcaagt cagaggtggc gaaacccgac aggactataa  16080
agataccagg cgtttccccc tggaagctcc ctcgtgcgct ctcctgttcc gaccctgccg  16140
cttaccggat acctgtccgc ctttctccct tcgggaagcg tggcgctttc tcatagctca  16200
cgctgtaggt atctcagttc ggtgtaggtc gttcgctcca agctgggctg tgtgcacgaa  16260
ccccccgttc agcccgaccg ctgcgcctta tccggtaact atcgtcttga gtccaacccg  16320
gtaagacacg acttatcgcc actggcagca gccactggta acaggattag cagagcgagg  16380
tatgtaggcg gtgctacaga gttcttgaag tggtggccta actacggcta cactagaagg  16440
acagtatttg gtatctgcgc tctgctgaag ccagttacct tcggaaaaag agttggtagc  16500
tcttgatccg gcaaacaaac caccgctggt agcggtggtt tttttgtttg caagcagcag  16560
attacgcgca gaaaaaaagg atctcaagaa gatccggaaa acgcaagcgc aaagagaaag  16620
caggtagctt gcagtgggct tacatggcga tagctagact gggcggtttt atggacagca  16680
agcgaaccgg aattgcc                                                 16697
```

<210> SEQ ID NO 2
<211> LENGTH: 20318
<212> TYPE: DNA
<213> ORGANISM: Artificial Sequence
<220> FEATURE:
<223> OTHER INFORMATION: vector

<400> SEQUENCE: 2

```
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgacct    240
gcaggtccta ggctctaatg aggtgggctg tcgttcattg gttaaagtgg gatcttcttt    300
ccctagattt ttttttttat tctgcctacc ctaatccccc atcttttgct ttctagagac    360
cagcaaatca aaaggataat atcgtctttt gacctctctc aattattgat ttatttctta    420
gatattttct tttgcctttt ttttttcaca cagcaaatca aatcatattt ttagaaagca    480
tatttttaag aggtaagata tggttgtggg gatgatggga atataaatca taatttctaa    540
agatttctaa acttcttaat tgatcacatc tcatattgaa ggttattatg tgtcatattt    600
gattggctgg tagtgtcgca tcagcataaa ttaaggtgtt agaatagacg taccaactcg    660
ataaaaaatt cagacattaa tttgatattg ttggacaagt ttaggggaca aactacaaat    720
tatagattta tatgttgtta gagaatataa gttttattat tatacagttt taagttttaa    780
acagtttttg taaggtaatt taaaatatcc gttaagctca caagaaaaaa ttatattcaa    840
ttaaaatttc aatcaaaagt tagcaatgaa tattttcatt gaagctctca tggcttgagc    900
ccttgaattt aatttttaca tcaaatcttt gatgatacgt taagtaatga tgcgatgaat    960
aacgtagtga ttgacataaa aaaatggttg ttatattttt attaggggtt aaattatttt   1020
gtaattcttt tccacgagag agtttttcaa atttataaat tttttttcaa tcctaagaat   1080
ctaaataata tgaaaattaa taaaacacga attttaaaat actctcaaaa aatattaaaa   1140
aaatcattta catataaatc aaatatctat aaaatactct acttattatc caaattgaag   1200
tgtcgaatat gggcgttgat tgagttttag ttcgattagt atcgatattg ttgtcaatgt   1260
aggaaggcgt acctacttaa gggatgaaat ggactataag tagttctaaa cattgtataa   1320
aaacatatgt aaatatcaaa cacaaatact tttaaaaaaa ttcctactcg aagccaccat   1380
acaaatagat atgaacgtcg tagaatccaa agagagaatt tgatagtcaa gttattataa   1440
aagcatgaag aacccagaaa ataatctcaa gtgcaagtcc ctatcaaatt tatcatacat   1500
aaaattccag ccaaacacta tctttttcac aagtgagaaa aaaatatcaa cttggtttac   1560
atccctccaa tcaaatcctc attcctggta ggtcacaatt tttctgacca ttttaaataa   1620
ataaatgtcg tttgtagaaa tgattaacta gtggatagtg atgtttttgt ccataaattc   1680
taaagtttca tgatatttat atatatcata aaaaatataa tatctatttt taaatacttt   1740
tatttagatt taacaattaa actattacga caaatttata tgaaacataa ttaaaatatc   1800
aacataaaca cttgtaagtt aaccaaactg tctcacgacg ttttgataac ttcgtataat   1860
gtatgctata cgaagttatg tttcccgatc aaatctgagg gacgttaaag cgatgataaa   1920
ttggaaccag aatatagaat ctttgttctg ctctagcttt tcttctgtac attttttacg   1980
attagactat gattttcatt caataaccaa aattctgaag tttgtcatca agttgctcaa   2040
tcaaacttgt accggtttgt ttcggtttta tatcagctca ctgttacact ttaaccaaaa   2100
tcggtttatg tcttaataaa ggaattgagt cggtttaact catatccgta ccaatgcgac   2160
gtcgtgtccg cgtttcagta gctttgctca ttgtcttcta cgggaacttt cccggacata   2220
ggaaccgccc tttcgttatc ctcatccatc gtgaaatcag gaaataaatg ttcgaagatt   2280
```

```
tgaggtcaaa agtcgaattt catgttgtct cttctattta gatacaaaat tgaagcaatt   2340
ttcaccaatt taatgccaaa atttaaaaca acgctgataa agtgaaactt gattcgattt   2400
atatttcaac cgaaactgct gaagcaagaa gaaaaagcgt aattacacat aacaagaacg   2460
ctaccgcaaa ctactaaacg ccaaacccaa tacaaaagta aaacgcagac gcttaagtga   2520
gaaacccaga aaacacaaac gcggatcggg ggatccacta gttctagagc ttaattcttg   2580
acgaaagtgc tcagcacatc gaagtagtcg gggaaggtct tccgggtgca cccagggtcc   2640
cggatggtga cggggacctc ggcacaggcg gcaagggaga aagccatcgc catcctgtgg   2700
tcgtcgtacg tgtcgatcgc cgtcacgttc agcttctccg gcggcgtgat gatgcagtag   2760
tccggccctt cctcaacaga tgctcccagc ttggttagct ccgtccggat cgcaaccatc   2820
ctctcggtct cctttactct ccaggaagcc acgtctctga tggctgtcgg gccatcggca   2880
aagagggcaa ccacagcaag agtcatggcg acatcaggca tcttgttcat gttgacatca   2940
atcgccttga ggtgtttcct cccaaatggc tcccgcggtg ggccagtaac agttacgcta   3000
gtctcggtcc atgtaacctt cgctcccatc atctccagta cctcagcaaa cttcacatca   3060
ccctgcaaac tggtggtgcc acaaccttcc acagtcacag tccctccagt aattgcagca   3120
ccagccaaga aatagcttgc gcttgaggca tcaccttcaa cataggcatt tttaggggac   3180
ttgtattttt gacctccctt aatgtagaat ctgtcccagc tatcagaatg ctctgctttc   3240
acaccaaaac gctccatcaa tctcaatgtc atttcgacgt acggaatgga gattaattta   3300
tcaatgattt caatctccac atccccaaga gccaaaggag cagccatcag caaggcactc   3360
aagtactgac tgctgatgga gccagacagc ttgaccttgc caccaggtag ccctccgatt   3420
ccattgacac gaacaggtgg gcagtcagtg ccaaggaaac aatcaacatc tgcaccaagc   3480
tgcttcaatc cgacaaccaa gtcgccaatg ggtctctccc tcattcttgg tactccatca   3540
agcacgtaag ttgcatttcc accagcagca gtaacagctg ctgtcaagga ccgcattgcg   3600
attccagcat tccccaagaa gagctgcact tcctctttag catcctcaac tgggaacttt   3660
ccaccacagc caacaactac agctcttttg gcagctttgt ccgcttcgac agagagacca   3720
agagtcctca aggccccgag catgtagtgg acatcctcac tgttcagcag gttatcaacc   3780
actgttgtcc cctcggacag ggcggcgagt aggaggatcc ggttggaaag cgacttggac   3840
cccggcagct tgacggtgcc ggagatctcc ttgatgggct gcagcacgat ctcctcggcg   3900
ccggccatgc accggatcct tccgccgttg ctgacgttgc cgaggcttct ggaggagcgg   3960
cgggcgacgg ggaggctggc ggtggacttg agcccctgga acggagcgac ggcggtggcc   4020
gacgaggcca tcatcacggt gggcgccata gacagcggcg gcaggtacga cagcgtctcg   4080
aacttcttgt tgccgtaggc cggccacacc tgcatacatt gaactcttcc accgttgctg   4140
ggaagggtgg agaagtcgtt agccttcttg gtggtgggga aggcggcgtt ggacttaagg   4200
ccggtgaacg gagccaccat gttggcctga gcaggggcgg tccggctaac ggtcgcgact   4260
gaggaggaga tcgaagccat tgtgatctgc gcatttaaca agaaattgaa cagtcaattg   4320
gggattttca ttatccataa ctaaattttg aagaaattgg aatactaaac gtcaccactt   4380
aaaaccctaa tccagatgaa tcgttatcga accagatata accaaaaggg gcaaaattga   4440
ctcgaaaacc ctagttctcg atacacggct aggtaatgac aatcgcacac agacaaatct   4500
ggttatacag aacttcgaag caagaaaaaa acgatgaaga atggatcatc caataaatcg   4560
actagactca atcttcacag gtttatcgat ccagcaaact taaaagacgg acctttattt   4620
tcaaactgga atgggacaaa acccgaaact ctattgtcgt aaaatcagat cgcggagaca   4680
```

```
gtaacagaaa aaacattaaa aagtaatgga aagacctaaa cccctgatct aattacaaac   4740

aaatcatacc tgttcttcgc ctgaggggtt cgaaatcgat aagcttggat cctctagagt   4800

cgagagaaat tgatgtctgt agaagaagaa gaacggttaa gagtagattt gggtgagaaa   4860

gatgtgaaat tgtttttata ggcaaagacg gagagtctat tttttgagca atcagatcgc   4920

atattaaatc taacggctga gatatcgatc cgtgtgtaca ataaaatgat gtataaaccg   4980

tcgatctgtt ttaatcgacg gttcatatta gtgatccgcg tgatggcagt gatagccact   5040

aagaatcgtc ttttgtttta catgtggcgc cacaaattag ggtaatgaag cggcaatatt   5100

ttggaactcg gaaaataaaa ttgcgccatc acattatttg aaaattttca catgctttta   5160

ttttaaaaac ccacgaatta caagttacaa ccgaaaaaga tttataatat agtgatttat   5220

actaattttg tagtagctta atgtatattg atactggaaa aacaatgaca atcatatgtt   5280

agtattatca agttatcgta ttgatattga tattggaaca tacaatgggt attgccttct   5340

ttcgaccata aatatcacca aatttacaaa gtttgtgtat accaagttat caattgtaaa   5400

tgggatgtca acattttaat ttccctttga gaaactatag accacaagaa cacacttcaa   5460

tagataaagt aactatttac ataagaggtt ttaaaatcac attaacaaaa ataattacca   5520

accggcactc acaaatacaa acagagcaca cgacatgtca aagccacaag taaattcgtt   5580

gagtggtggt ttcattacaa ttgtgtcact tgcagcacaa actatcttgc tctgggaatc   5640

atctcagcat caaagatcat gctcacttca ggggaactta gtgtatccat gcctcgactc   5700

atatttctcc tcgacaaaca taacttcgta taatgtatgc tatacgaagt tatattaata   5760

agctttaggg ataacagggt aatgatatcg aattccccga tcaaatctga gggacgttaa   5820

agcgatgata aattggaacc agaatataga atctttgttc tgctctagct tttcttctgt   5880

acatttttta cgattagact atgattttca ttcaataacc aaaattctga agtttgtcat   5940

caagttgctc aatcaaactt gtaccggttt gtttcggttt tatatcagct cactgttaca   6000

ctttaaccaa aatcggttta tgtcttaata aaggaattga gtcggtttaa ctcatatccg   6060

taccaatgcg acgtcgtgtc cgcgtttcag tagctttgct cattgtcttc tacgggaact   6120

ttcccggaca taggaaccgc cctttcgtta tcctcatcca tcgtgaaatc aggaaataaa   6180

tgttcgaaga tttgaggtca aaagtcgaat ttcatgttgt ctcttctatt tagatacaaa   6240

attgaagcaa ttttcaccaa tttaatgcca aaatttaaaa caacgctgat aaagtgaaac   6300

ttgattcgat ttatatttca accgaaactg ctgaagcaag aagaaaaagc gtaattacac   6360

ataacaagaa cgctaccgca aactactaaa cgccaaaccc aatacaaaag taaaacgcag   6420

acgcttaagt gagaaaccca gaaaacacaa acgcggatcg gggcgcgcc acgcgtgcta    6480

gcttttaatc agcggtcaaa acccctctac gaacttgatc cctctctatc gattcgaaaa   6540

gtgctttgaa gttccattct ccgaagccat cgtccccttt acgctgaatg aactcaaaga   6600

aaacgggtcc catgagagtc tcggaaaaga tttgtaacag gagcctctta tcaccctcaa   6660

ccgaagaacc atcgagaagt ataccccctgg cttgcagttg gtccacgggt tccccatgat   6720

caggcaggcg tccttctagc atctcatagt aagtatcggg aggtgcagtc atgaatctca   6780

tacctatctt cttcaatgca tcccaggttt tcacaagatc atcagtcaga aaagcgacat   6840

gctgaatgcc ttcaccattg aactgcataa gaaactcttc gatttgtcct gcacctttgc   6900

ttgactcttc gttgagtgga atccttatca taccatctgg agcgctcata gcctttgatg   6960

tgagaccagt atactctcct ttgatgtcaa agtatctagc ttccctaaag ttgaagagtt   7020
```

-continued

```
tctcatagaa gttagcccag tataccattc gtccacgata gacgttgtgt gtcaaatgat   7080
caataacctt caagccagca ccgacaggat ttcgttccac gccttcaaga tagacgaaat   7140
ctatgtcgta gatagaactg ccctctccga atctgtcgat aagatacaac ggtgcaccac   7200
cgatgccttt gatggctgga agattcaatt ccataggtcc agtgtcaatg tgaataggct   7260
gagctccaag ttctaatgcc ctattgtagg ctttctggga atccttaact cgaaatgcca   7320
tgccacaaac ggatggtcca tgttcggcag caaagtagct tgctatagag ttaggttcgt   7380
tgttcaagat caggttaatc tctccttgcc gatataggtg cacgttctta ctgcgatgtg   7440
tagctacctt agtaaacccc ataatctcaa agatgggttc aagggtccca ggtgtaggag   7500
aagcaaactc aatgaactcg aaacccatga gtcccatagg attctcgtat agatcagcca   7560
tgcatctaat cctacctccg ttgctaacat tccccagcga tctggaagat ctccgagcaa   7620
ctggcaaact agcagtactc ttcaaccctt gaaatggtgc cacagctgtg gcagagctgg   7680
ccatcatcac agtgggagcc atagatagcg gaggtaagta ggataaggtc tcaaacttct   7740
tgttgccata ggctggccag acttgcatat actgtactct cccaccgttg ctcggaagtg   7800
ttgagaagtc attagccttc ttagtggttg gaaatgcagc atttgactta agacctgtga   7860
acggagccac catattagct tgggctggtg cggtacgtga aacagtggca actgaagatg   7920
aaatactagc catggttttg gtttaataag aagagaaaag agttcttttg ttatggctga   7980
agtaatagag aaatgagctc gagtcctctc caaatgaaat gaacttcctt atatagagga   8040
agggtcttgc gaaggatagt gggattgtgc gtcatccctt acgtcagtgg agatatcaca   8100
tcaatccact tgctttgaag acgtggttgg aacgtcttct tttccacga tgctcctcgt   8160
gggtgggggt ccatctttgg gaccactgtc ggcaggggca tcttgaacga tagcctttcc   8220
tttatcgcaa tgatggcatt tgtaggtgcc accttccttt tctactgtcc ttttgatgaa   8280
gtgacagata gctgggcaat ggaatccgag gaggtttccc gatattaccc tttgttgaaa   8340
agtctcaata gccctttggt cttctgagac tgtatctttg atattcttgg agtagacgag   8400
agtgtcgtgc tccaccatgt tgcggccgcc ctgcaggtac gtagcgatcg cgtaaataat   8460
tttaattagg cacggcataa aaatagtgct ctcaaaattc atattaaaca aattattaac   8520
atttaatatt gtttttgtat aattttatat cattttaaac acgtaaaata taacacaaaa   8580
atatttataa atgatttgcc taatgtagaa actataattt tgtttcaatt atatatatat   8640
aattttgatt ttgatttaat tgtaaatatt ttaaaaacta aatcaatcaa ataaaattca   8700
tgttaggtat ataatttttt tcctaaaatg atgctacatc gagtacgatg ttaattattt   8760
gtgaaaattg agctaaattt aatatttatg tattaaattg tataaaatca aagttcgtat   8820
atcaaattga atattaaatc ataatttata tataattttg atatataccc cttaattatg   8880
ataaaaaaaa agttttgtat tttaatttat acaaataatc ttctaaattt aatcccaaac   8940
ttttaatttt ttttttgaac atcaatatca tttgctattt tggatacaat atctaaaact   9000
acccataacc ccttcctaat ccttaaatag gaggataatg ctctaaagca tactcgaacc   9060
cacatcattt cacactgata acaacactaa tactaatcta attaagactc aatcgtcccg   9120
atacttaatt taataacatt gcattgttgt ctaataatcc aatcctttat tttttattt   9180
ttttctgaaa agcctttaaa agtaaattct caacttcagt actttaaatt atattttata   9240
tctatgctta ggtgtcatca aaacaaaccc tttaaattct aaataaagat atagttatag   9300
atatgattga ttgttaaggt ccaaaaacaa actaagtcaa atctcaaaca atcatgtagc   9360
atgttgaatt tttttaatg gatatatttt tggattcatt cataatggta aagtttaaaa   9420
```

```
gtatttttgt cgactaagtc ttaatttgat tagtatggca ttatcgttaa tataggagaa   9480
tgtgagttcg agtgcgttga aacgcagtta aagagggact atagatgatt ttaagtattg   9540
tgttaaaaat aacagatata atgagaatgt ataataataa aattattaaa aataaatttg   9600
aaattttttt ctaaaataat ttttcaaagt aaataaaaaa ccattaataa ctttttaaaa   9660
tggtattttt tgaaaaaaat actttttata taaaaatttt aagttatttt aattatttta   9720
aatataaaaa acttatttct atattataaa aatttaaatt aatcataaaa taaaaaaaaa   9780
tagaattcca ttaagttaaa gtttcatttt ttagatagtc caaacacatg gattcgattc   9840
gttttattta tttatttatt tattcagcac acaagaaaaa atatttaaaa aatcaaccaa   9900
aatgaaggtg gttaggggtg tatgtgcaaa tccattgcca ttagcccatt atcaaagccc   9960
accaacccta tgttaccaac attttattta ttcttttaaa tatgtattcg aaactcgtat  10020
tcaactcatt cgtaaatatg aaaatatgat atatatatat gactcccgaa tacataaaat  10080
cctaaaaaaa tttagtatat ctacgttgac aagtatttat attcattaat cacactaaaa  10140
ctcgaataat ataatacgat atatgacatc taaacataga attactcaaa gcaaccgcta  10200
atagactata cgacttgtgt aggagttaca aacaaggtag ttaatattac actgatggct  10260
caacggttac aacatattta cgagctaagt tgagttatgg tccaattctt aaaaagaaaa  10320
aaaaggttga atttaactca acttgatcca ttcaaataat tacgggtaag taaaacttga  10380
ttcaatttaa aaaataaaaa taaaaaattg ttcgaatttc aagttaattg aattgcatta  10440
tttgagttat tcaatttttt ttttcaaatc aatttgaaca agtattagaa attgcgtgac  10500
tcaaattcct gttaaaaata aaattaaaac cgcgatcgcc atggagccat ttacaattga  10560
atatatcctg ccgccgctgc cgctttgcac ccggtggagc ttgcatgttg gtttctacgc  10620
agaactgagc cggttaggca gataatttcc attgagaact gagccatgtg caccttcccc  10680
ccaacacggt gagcgacggg gcaacggagt gatccacatg ggacttttaa acatcatccg  10740
tcggatggcg ttgcgagaga agcagtcgat ccgtgagatc agccgacgca ccgggcaggc  10800
gcgcaacacg atcgcaaagt atttgaacgc aggtacaatc gagccgacgt tcacggtacc  10860
ggaacgacca agcaagctag cttagtaaag ccctcgctag attttaatgc ggatgttgcg  10920
attacttcgc caactattgc gataacaaga aaaagccagc ctttcatgat atatctccca  10980
atttgtgtag ggcttattat gcacgcttaa aaataataaa agcagacttg acctgatagt  11040
ttggctgtga gcaattatgt gcttagtgca tctaacgctt gagttaagcc gcgccgcgaa  11100
gcggcgtcgg cttgaacgaa ttgttagaca ttatttgccg actaccttgg tgatctcgcc  11160
tttcacgtag tggacaaatt cttccaactg atctgcgcgc gaggccaagc gatcttcttc  11220
ttgtccaaga taagcctgtc tagcttcaag tatgacgggc tgatactggg ccggcaggcg  11280
ctccattgcc cagtcggcag cgacatcctt cggcgcgatt ttgccggtta ctgcgctgta  11340
ccaaatgcgg gacaacgtaa gcactacatt tcgctcatcg ccagcccagt cgggcggcga  11400
gttccatagc gttaaggttt catttagcgc ctcaaataga tcctgttcag gaaccggatc  11460
aaagagttcc tccgccgctg gacctaccaa ggcaacgcta tgttctcttg cttttgtcag  11520
caagatagcc agatcaatgt cgatcgtggc tggctcgaag atacctgcaa gaatgtcatt  11580
gcgctgccat tctccaaatt gcagttcgcg cttagctgga taacgccacg gaatgatgtc  11640
gtcgtgcaca acaatggtga cttctacagc gcggagaatc tcgctctctc caggggaagc  11700
cgaagtttcc aaaaggtcgt tgatcaaagc tcgccgcgtt gtttcatcaa gccttacggt  11760
```

```
caccgtaacc agcaaatcaa tatcactgtg tggcttcagg ccgccatcca ctgcggagcc  11820
gtacaaatgt acggccagca acgtcggttc gagatggcgc tcgatgacgc caactacctc  11880
tgatagttga gtcgatactt cggcgatcac cgcttccctc atgatgttta actttgtttt  11940
agggcgactg ccctgctgcg taacatcgtt gctgctccat aacatcaaac atcgacccac  12000
ggcgtaacgc gcttgctgct tggatgcccg aggcatagac tgtaccccaa aaaaacagtc  12060
ataacaagcc atgaaaaccg ccactgcgcc gttaccaccg ctgcgttcgg tcaaggttct  12120
ggaccagttg cgtgagcgca tacgctactt gcattacagc ttacgaaccg aacaggctta  12180
tgtccactgg gttcgtgcct tcatccgttt ccacggtgtg cgtcacccgg caaccttggg  12240
cagcagcgaa gtcgaggcat ttctgtcctg gctggcgaac gagcgcaagg tttcggtctc  12300
cacgcatcgt caggcattgg cggccttgct gttcttctac ggcaaggtgc tgtgcacgga  12360
tctgccctgg cttcaggaga tcggaagacc tcggccgtcg cggcgcttgc cggtggtgct  12420
gaccccggat gaagtggttc gcatcctcgg ttttctggaa ggcgagcatc gtttgttcgc  12480
ccagcttctg tatggaacgg gcatgcttgc ttggtcgttc cggtaccgtg aacgtcggct  12540
cgattgtacc tgcgttcaaa tactttgcga tcgtgttgcg cgcctgcccg gtgcgtcggc  12600
tgatctcacg gatcgactgc ttctctcgca acgccatccg acggatgatg tttaaaagtc  12660
ccatgtggat cactccgttg ccccgtcgct caccgtgttg gggggaaggt gcacatggct  12720
cagttctcaa tggaaattat ctgcctaacc ggctcagttc tgcgtagaaa ccaacatgca  12780
agctccaccg ggtgcaaagc ggcagcggcg gcaggatata ttcaattgta aatggctcca  12840
tgcgttaatt aagcttgaga ggcggtttgc gtattggcta gagcagcttg ccaacatggt  12900
ggagcacgac actctcgtct actccaagaa tatcaaagat acagtctcag aagaccaaag  12960
ggctattgag acttttcaac aaagggtaat atcgggaaac ctcctcggat tccattgccc  13020
agctatctgt cacttcatca aaaggacagt agaaaaggaa ggtggcacct acaaatgcca  13080
tcattgcgat aaaggaaagg ctatcgttca agatgcctct gccgacagtg gtcccaaaga  13140
tggaccccca cccacgagga gcatcgtgga aaaagaagac gttccaacca cgtcttcaaa  13200
gcaagtggat tgatgtgaac atggtggagc acgacactct cgtctactcc aagaatatca  13260
aagatacagt ctcagaagac caaagggcta ttgagacttt tcaacaaagg gtaatatcgg  13320
gaaacctcct cggattccat tgcccagcta tctgtcactt catcaaaagg acagtagaaa  13380
aggaaggtgg cacctacaaa tgccatcatt gcgataaagg aaaggctatc gttcaagatg  13440
cctctgccga cagtggtccc aaagatggac ccccacccac gaggagcatc gtggaaaaag  13500
aagacgttcc aaccacgtct tcaaagcaag tggattgatg tgatatctcc actgacgtaa  13560
gggatgacgc acaatcccac tatccttcgc aagacccttc ctctatataa ggaagttcat  13620
ttcatttgga gaggacacgc tgaaatcacc agtctctctc tacaaatcta tctctctcga  13680
gctttcgcag atctgtcgaa ccaccatggc accgaagaag aagcgcaagg tgcatatgaa  13740
caccaagtac aacaaggagt tcctgctcta cctggcgggc ttcgtggacg gggacggctc  13800
catcatcgcc cagatcaagc cgaaccagtc ctacaagttc aagcatcagc tgtccctcac  13860
cttcaccgtc acccagaaga cacagcgccg ttggttcctc gacaagctgg tggacgagat  13920
cggagtgggc tacgtgtacg accagggcag cgtctcccac taccgcctgt cccagatcaa  13980
gcctctgcac aacttcctga cccagctcca gcccttcctg aagctcaagc agaagcaggc  14040
caacctcgtg ctgaagatca tcgagcagct gccctccgcc aaggaatccc cggacaagtt  14100
cctggaggtg tgcacgtggg tggaccagat cgcggccctc aacgacagca agacccgcaa  14160
```

gacgacctcg gagacggtgc gggcggtcct ggactccctc ccaggatccg tgggaggtct 14220
atcgccatct caggcatcca gcgccgcatc ctcggcttcc tcaagcccgg gttcagggat 14280
ctccgaagca ctcagagctg gagcaactaa gtccaaggaa ttcctgctct acctggcggg 14340
cttcgtcgac ggggacggct ccatcaaggc cgcgatcaag ccgaaccagt cctacaagtt 14400
caagcatcag ctgtccctca ccttccaggt cacgcagaag acacagcgcc gttggttcct 14460
cgacaagctg gtggacgaga tcggggtggg ctacgtgtac gactccggca gcgtctccga 14520
ctaccagctg tcccagatca agcctctgca caacttcctg acccagctcc agcccttcct 14580
gaagctcaag cagaagcagg ccaacctcgt gctgaagatc atcgagcagc tgccctccgc 14640
caaggaatcc ccggacaagt tcctggaggt gtgcacctgg gtggaccaga tcgccgctct 14700
gaacgactcc aagacccgca agaccacttc cgagaccgtc cgcgccgttc tagacagtct 14760
ctccgagaag aagaagtcgt ccccctagca tgccgttcaa acatttggca ataaagtttc 14820
ttaagattga atcctgttgc cggtcttgcg atgattatca tataatttct gttgaattac 14880
gttaagcatg taataattaa catgtaatgc atgacgttat ttatgagatg ggtttttatg 14940
attagagtcc cgcaattata catttaatac gcgatagaaa acaaaatata gcgcgcaaac 15000
taggataaat tatcgcgcgc ggtgtcatct atgttactag atcgggccca ctagtcgacc 15060
gcatgactta attaagtcat gcggtcgact agtgcaggtc gacggccgag tactggcagg 15120
atatataccg ttgtaatttg tcgcgtgtga ataagtcgct gtgtatgttt gtttgattgt 15180
ttctgttgga gtgcagccca tttcaccgga caagtcggct agattgattt agccctgatg 15240
aactgccgag gggaagccat cttgagcgcg gaatgggaat ggatttcgtt gtacaacgag 15300
acgacagaac acccacgggc tccaaggatc gggccttgat gttacccgag agcttggcac 15360
ccagcctgcg cgagcaggat cgatccaacc cctccgctgc tatagtgcag tcggcttctg 15420
acgttcagtg cagccgtctt ctgaaaacga catgtcgcac aagtcctaag ttacgcgaca 15480
ggctgccgcc ctgccctttt cctggcgttt tcttgtcgcg tgttttagtc gcataaagta 15540
gaatacttgc gactagaacc ggagacatta cgccatgaac aagagcgccg ccgctggcct 15600
gctgggctat gcccgcgtca gcaccgacga ccaggacttg accaaccaac gggccgaact 15660
gcacgcggcc ggctgcacca agctgttttc cgagaagatc accggcacca ggcgcgaccg 15720
cccggagctg gccaggatgc ttgaccacct acgccctggc gacgttgtga cagtgaccag 15780
gctagaccgc ctggcccgca gcacccgcga cctactggac attgccgagc gcatccagga 15840
ggccggcgcg ggcctgcgta gcctggcaga gccgtgggcc gacaccacca cgccggccgg 15900
ccgcatggtg ttgaccgtgt tcgccggcat tgccgagttc gagcgttccc taatcatcga 15960
ccgcacccgg agcgggcgcg aggccgccaa ggcccgaggc gtgaagtttg gcccccgccc 16020
taccctcacc ccggcacaga tcgcgcacgc ccgcgagctg atcgaccagg aaggccgcac 16080
cgtgaaagag gcggctgcac tgcttggcgt gcatcgctcg accctgtacc gcgcacttga 16140
gcgcagcgag gaagtgacgc ccaccgaggc caggcggcgc ggtgccttcc gtgaggacgc 16200
attgaccgag gccgacgccc tggcggccgc cgagaatgaa cgccaagagg aacaagcatg 16260
aaaccgcacc aggacggcca ggacgaaccg tttttcatta ccgaagagat cgaggcggag 16320
atgatcgcgg ccgggtacgt gttcgagccg cccgcgcacg tctcaaccgt gcggctgcat 16380
gaaatcctgg ccggtttgtc tgatgccaag ctggcggcct ggccggccag cttggccgct 16440
gaagaaaccg agcgccgccg tctaaaaagg tgatgtgtat ttgagtaaaa cagcttgcgt 16500

```
catgcggtcg ctgcgtatat gatgcgatga gtaaataaac aaatacgcaa ggggaacgca  16560
tgaaggttat cgctgtactt aaccagaaag gcgggtcagg caagacgacc atcgcaaccc  16620
atctagcccg cgccctgcaa ctcgccgggg ccgatgttct gttagtcgat tccgatcccc  16680
agggcagtgc ccgcgattgg gcggccgtgc gggaagatca accgctaacc gttgtcggca  16740
tcgaccgccc gacgattgac cgcgacgtga aggccatcgg ccggcgcgac ttcgtagtga  16800
tcgacggagc gccccaggcg gcggacttgg ctgtgtccgc gatcaaggca gccgacttcg  16860
tgctgattcc ggtgcagcca agcccttacg acatatgggc caccgccgac ctggtggagc  16920
tggttaagca gcgcattgag gtcacggatg gaaggctaca agcggccttt gtcgtgtcgc  16980
gggcgatcaa aggcacgcgc atcggcggtg aggttgccga ggcgctggcc gggtacgagc  17040
tgcccattct tgagtcccgt atcacgcagc gcgtgagcta cccaggcact gccgccgccg  17100
gcacaaccgt tcttgaatca gaacccgagg gcgacgctgc ccgcgaggtc caggcgctgg  17160
ccgctgaaat taaatcaaaa ctcatttgag ttaatgaggt aaagagaaaa tgagcaaaag  17220
cacaaacacg ctaagtgccg gccgtccgag cgcacgcagc agcaaggctg caacgttggc  17280
cagcctggca gacacgccag ccatgaagcg ggtcaacttt cagttgccgg cggaggatca  17340
caccaagctg aagatgtacg cggtacgcca aggcaagacc attaccgagc tgctatctga  17400
atacatcgcg cagctaccag agtaaatgag caaatgaata aatgagtaga tgaattttag  17460
cggctaaagg aggcggcatg gaaaatcaag aacaaccagg caccgacgcc gtggaatgcc  17520
ccatgtgtgg aggaacgggc ggttggccag gcgtaagcgg ctgggttgtc tgccggccct  17580
gcaatggcac tggaaccccc aagcccgagg aatcggcgtg acggtcgcaa accatccggc  17640
ccggtacaaa tcggcgcggc gctgggtgat gacctggtgg agaagttgaa ggccgcgcag  17700
gccgcccagc ggcaacgcat cgaggcagaa gcacgccccg gtgaatcgtg gcaagcggcc  17760
gctgatcgaa tccgcaaaga atcccggcaa ccgccggcag ccggtgcgcc gtcgattagg  17820
aagccgccca agggcgacga gcaaccagat tttttcgttc cgatgctcta tgacgtgggc  17880
acccgcgata gtcgcagcat catggacgtg gccgttttcc gtctgtcgaa gcgtgaccga  17940
cgagctggcg aggtgatccg ctacgagctt ccagacgggc acgtagaggt ttccgcaggg  18000
ccggccggca tggccagtgt gtgggattac gacctggtac tgatggcggt ttcccatcta  18060
accgaatcca tgaaccgata ccgggaaggg aagggagaca agcccggccg cgtgttccgt  18120
ccacacgttg cggacgtact caagttctgc cggcgagccg atggcggaaa gcagaaagac  18180
gacctggtag aaacctgcat tcggttaaac accacgcacg ttgccatgca gcgtacgaag  18240
aaggccaaga acggccgcct ggtgacggta tccgagggtg aagccttgat tagccgctac  18300
aagatcgtaa agagcgaaac cgggcggccg gagtacatcg agatcgagct agctgattgg  18360
atgtaccgcg agatcacaga aggcaagaac ccggacgtgc tgacggttca ccccgattac  18420
tttttgatcg atcccggcat cggccgtttt ctctaccgcc tggcacgccg cgccgcaggc  18480
aaggcagaag ccagatggtt gttcaagacg atctacgaac gcagtggcag cgccggagag  18540
ttcaagaagt tctgtttcac cgtgcgcaag ctgatcgggt caaatgacct gccggagtac  18600
gatttgaagg aggaggcggg gcaggctggc ccgatcctag tcatgcgcta ccgcaacctg  18660
atcgagggcg aagcatccgc cggttcctaa tgtacggagc agatgctagg gcaaattgcc  18720
ctagcagggg aaaaaggtcg aaaaggtctc tttcctgtgg atagcacgta cattgggaac  18780
ccaaagccgt acattgggaa ccggaacccg tacattggga acccaaagcc gtacattggg  18840
aaccggtcac acatgtaagt gactgatata aaagagaaaa aaggcgattt ttccgcctaa  18900
```

```
aactctttaa aacttattaa aactcttaaa acccgcctgg cctgtgcata actgtctggc  18960
cagcgcacag ccgaagagct gcaaaaagcg cctacccttc ggtcgctgcg ctccctacgc  19020
cccgccgctt cgcgtcggcc tatcgcggcc gctggccgct caaaaatggc tggcctacgg  19080
ccaggcaatc taccagggcg cggacaagcc gcgccgtcgc cactcgaccg ccggcgccca  19140
catcaaggca ccctgcctcg cgcgtttcgg tgatgacggt gaaaacctct gacacatgca  19200
gctcccggag acggtcacag cttgtctgta agcggatgcc gggagcagac aagcccgtca  19260
gggcgcgtca gcgggtgttg gcgggtgtcg gggcgcagcc atgacccagt cacgtagcga  19320
tagcggagtg tatactggct taactatgcg gcatcagagc agattgtact gagagtgcac  19380
catatgcggt gtgaaatacc gcacagatgc gtaaggagaa aataccgcat caggcgctct  19440
tccgcttcct cgctcactga ctcgctgcgc tcggtcgttc ggctgcggcg agcggtatca  19500
gctcactcaa aggcggtaat acggttatcc acagaatcag gggataacgc aggaaagaac  19560
atgtgagcaa aaggccagca aaaggccagg aaccgtaaaa aggccgcgtt gctggcgttt  19620
ttccataggc tccgcccccc tgacgagcat cacaaaaatc gacgctcaag tcagaggtgg  19680
cgaaacccga caggactata aagataccag gcgtttcccc ctggaagctc cctcgtgcgc  19740
tctcctgttc cgaccctgcc gcttaccgga tacctgtccg cctttctccc ttcgggaagc  19800
gtggcgcttt ctcatagctc acgctgtagg tatctcagtt cggtgtaggt cgttcgctcc  19860
aagctgggct gtgtgcacga accccccgtt cagcccgacc gctgcgcctt atccggtaac  19920
tatcgtcttg agtccaaccc ggtaagacac gacttatcgc cactggcagc agccactggt  19980
aacaggatta gcagagcgag gtatgtaggc ggtgctacag agttcttgaa gtggtggcct  20040
aactacggct acactagaag gacagtattt ggtatctgcg ctctgctgaa gccagttacc  20100
ttcggaaaaa gagttggtag ctcttgatcc ggcaaacaaa ccaccgctgg tagcggtggt  20160
tttttgttt gcaagcagca gattacgcgc agaaaaaaag gatctcaaga agatccggaa  20220
aacgcaagcg caaagagaaa gcaggtagct tgcagtgggc ttacatggcg atagctagac  20280
tgggcggttt tatggacagc aagcgaaccg gaattgcc                          20318
```

<210> SEQ ID NO 3
<211> LENGTH: 22
<212> TYPE: DNA
<213> ORGANISM: Gossypium hirsutum

<400> SEQUENCE: 3

```
taaaattatt tacaagtgtt ta                                              22
```

<210> SEQ ID NO 4
<211> LENGTH: 3687
<212> TYPE: DNA
<213> ORGANISM: Gossypium hirsutum

<400> SEQUENCE: 4

```
ccagtactaa aatccagatc atgcatggac ctgcaggtcg acggccgagt actgttttat     60
ttttaacagg aatttgagtc acgcaatttc taatacttgt tcaaattgat ttgaaaaaaa    120
aaattgaata actcaaataa tgcaattcaa ttaacttgaa attcgaacaa tttttttattt    180
ttattttta aattgaatca agttttactt acccgtaatt atttgaatgg atcaagttga    240
gttaaattca accttttttt tctttttaag aattggacca taactcaact tagctcgtaa    300
atatgttgta accgttgagc catcagtgta atattaacta ccttgtttgt aactcctaca    360
```

-continued

```
caagtcgtat agtctattag cggttgcttt gagtaattct atgtttagat gtcatatatc    420
gtattatatt attcgagttt tagtgtgatt aatgaatata aatacttgtc aacgtagata    480
tactaaattt ttttaggatt ttatgtattc gggagtcata tatatatatc atattttcat    540
atttacgaat gagttgaata cgagtttcga atacatattt aaaagaataa ataaaatgtt    600
ggtaacatag ggttggtggg ctttgataat gggctaatgg caatggattt gcacatacac    660
ccctaaccac cttcattttg gttgattttt taaatatttt ttcttgtgtg ctgaataaat    720
aaataaataa ataaaacgaa tcgaatccat gtgtttggac tatctaaaaa atgaaacttt    780
aacttaatgg aattctattt ttttttattt tatgattaat ttaaattttt ataatataga    840
aataagtttt ttatatttaa aataattaaa ataacttaaa atttttatat aaaaagtatt    900
tttttcaaaa aataccattt taaaaagtta ttaatggttt tttatttact ttgaaaaatt    960
attttagaaa aaaatttcaa atttattttt aataatttta ttattataca ttctcattat   1020
atctgttatt tttaacacaa tacttaaaat catctatagt ccctctttaa ctgcgtttca   1080
acgcactcga actcacattc tcctatatta acgataatgc catactaatc aaattaagac   1140
ttagtcgaca aaaatacttt taaactttac cattatgaat gaatccaaaa atatatccat   1200
taaaaaaaat tcaacatgct acatgattgt ttgagatttg acttagtttg tttttggacc   1260
ttaacaatca atcatatcta taactatatc tttatttaga atttaaaggg tttgttttga   1320
tgacacctaa gcatagatat aaaatataat ttaaagtact gaagttgaga atttactttt   1380
aaaggctttt cagaaaaaaa taaaaaaata aaggattgga ttattagaca acaatgcaat   1440
gttattaaat taagtatcgg gacgattgag tcttaattag attagtatta gtgttgttat   1500
cagtgtgaaa tgatgtgggt tcgagtatgc tttagagcat tatcctccta tttaaggatt   1560
aggaaggggt tatgggtagt tttagatatt gtatccaaaa tagcaaatga tattgatgtt   1620
caaaaaaaaa attaaaagtt tgggattaaa tttagaagat tatttgtata aattaaaata   1680
caaaactttt tttttatcat aattaagggg tatatatcaa aattatatat aaattatgat   1740
ttaatattca atttgatata cgaactttga ttttatacaa tttaatacat aaatattaaa   1800
tttagctcaa ttttcacaaa taattaacat cgtactcgat gtagcatcat tttaggaaaa   1860
aaattatata cctaacatga attttatttg attgatttag tttttaaaat atttacaatt   1920
aaatcaaaat caaaattata tatatataat tgaaacaaaa ttatagtttc tacattaggc   1980
aaatcattta taaatatttt tgtgttatat tttacgtgtt taaaatgata taaaattata   2040
caaaaacaat attaaatgtt aataatttgt ttaatatgaa ttttgagagc actattttta   2100
tgccgtgcct aattaaaatt atttacaagt gtttatgttg atattttaat tatgtttcat   2160
ataaatttgt cgtaatagtt taattgttaa atctaaataa aagtatttaa aaatagatat   2220
tatatttttt atgatatata taaatatcat gaaactttag aatttatgga caaaaacatc   2280
actatccact agttaatcat ttctacaaac gacatttatt tatttaaaat ggtcagaaaa   2340
attgtgacct accaggaatg aggatttgat tggagggatg taaaccaagt tgatattttt   2400
ttctcacttg tgaaaaagat agtgtttggc tggaatttta tgtatgataa atttgatagg   2460
gacttgcact tgagattatt ttctgggttc ttcatgcttt tataataact tgactatcaa   2520
attctctctt tggattctac gacgttcata tctatttgta tggtggcttc gagtaggaat   2580
tttttaaaa gtatttgtgt ttgatattta catatgtttt tatacaatgt ttagaactac   2640
ttatagtcca tttcatccct taagtaggta cgccttccta cattgacaac aatatcgata   2700
ctaatcgaac taaaactcaa tcaacgccca tattcgacac ttcaatttgg ataataagta   2760
```

```
gagtatttta tagatatttg atttatatgt aaatgatttt tttaatattt tttgagagta   2820

ttttaaaatt cgtgttttat taattttcat attatttaga ttcttaggat tgaaaaaaaa   2880

tttataaatt tgaaaaactc tctcgtggaa aagaattaca aaataattta acccctaata   2940

aaaatataac aaccattttt ttatgtcaat cactacgtta ttcatcgcat cattacttaa   3000

cgtatcatca aagatttgat gtaaaaatta aattcaaggg ctcaagccat gagagcttca   3060

atgaaaatat tcattgctaa cttttgattg aaattttaat tgaatataat tttttcttgt   3120

gagcttaacg gatattttaa attaccttac aaaaactgtt taaaacttaa aactgtataa   3180

taataaaact tatattctct aacaacatat aaatctataa tttgtagttt gtcccctaaa   3240

cttgtccaac aatatcaaat taatgtctga attttttatc gagttggtac gtctattcta   3300

acaccttaat ttatgctgat gcgacactac cagccaatca aatatgacac ataataacct   3360

tcaatatgag atgtgatcaa ttaagaagtt tagaaatctt tagaaattat gatttatatt   3420

cccatcatcc ccacaaccat atcttacctc ttaaaaatat gctttctaaa aatatgattt   3480

gatttgctgt gtgaaaaaaa aaaggcaaaa gaaaatatct aagaaataaa tcaataattg   3540

agagaggtca aaagacgata ttatcctttt gatttgctgg tctctagaaa gcaaaagatg   3600

ggggattagg gtaggcagaa taaaaaaaaa aatctaggga aagaagatcc cactttaacc   3660

aatgaacgac agcccacctc attagag                                       3687
```

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5

```
tccagtacta aaatccagat catgc                                           25
```

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6

```
tgatgcgatg aataacgtag tg                                              22
```

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7

```
cgacagccat cagagacgtg                                                 20
```

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gacccttgaa cccatctttg 20

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
caaaatattg ccgcttcatt accc 24

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
gcatcaaaga tcatgctcac ttc 23

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
gaaacagtgg caactgaaga tgaaatac 28

<210> SEQ ID NO 12
<211> LENGTH: 262
<212> TYPE: DNA
<213> ORGANISM: Artificial sequence
<220> FEATURE:
<223> OTHER INFORMATION: stacked event figure 2a

<400> SEQUENCE: 12
ttgtttaata tgaattttga gagcactatt tttatgccgt gcctaattaa aattatttac 60
cggcaggata tattcaattg taaatggctc catggcgatc gctacaacca aactgtctca 120
cgacgttttg ataacttcgt ataatgtatg ctatacgaag ttatgtttcc cgatcaaatc 180
tgagggacgt taaagcgatg ataaattgga accagaatat agaatctttg ttctgctctt 240
tctgtacatt ttttacgatt ag 262

<210> SEQ ID NO 13
<211> LENGTH: 255
<212> TYPE: DNA
<213> ORGANISM: Artificial sequence
<220> FEATURE:
<223> OTHER INFORMATION: targeted insertion event cons. 93-23

<400> SEQUENCE: 13
ttgtttaata tgaattttga gagcactatt tttatgccgt gcctaattaa aatttgatgt 60
caattgtaaa tggctccatg gcgatcgcta caaccaaact gtctcacgac gttttgataa 120
cttcgtataa tgtatgctat acgaagttat gtttcccgat caaatctgag ggacgttaaa 180
gcgatgataa attggaacca gaatatagaa tctttgttct gctctagctt ttcttctgta 240 catttttac gatta 255

<210> SEQ ID NO 14
<211> LENGTH: 111
<212> TYPE: DNA
<213> ORGANISM: Artificial sequence
<220> FEATURE:
<223> OTHER INFORMATION: targeted insertion event cons. 91-74

<400> SEQUENCE: 14
ttgtttaata tgaattttga aggcactatt tttatgccgt gcctaattgg aaccagaata 60
tagaatcttt gttctgctct agcttttctt ctgtacattt tttacgatta g 111

<210> SEQ ID NO 15
<211> LENGTH: 245
<212> TYPE: DNA
<213> ORGANISM: Artificial sequence
<220> FEATURE:
<223> OTHER INFORMATION: targeted insertion event cons. 92-13

<400> SEQUENCE: 15
ttgtttaata tgaattttga gagcactatt tttatgccgt gcctaattaa aattataaat 60
ggctccatgg cgatcgctac aaccaaactg tctcacgacg ttttgataac ttcgtataat 120
gtatgctata cgaagttatg tttcccgatc aaatctgagg gacgttaaag cgatgataaa 180
ttggaaccag aatatagaat ctttgttctg ctctagcttt tcttctgtac atttttttacg 240 attag 245

<210> SEQ ID NO 16
<211> LENGTH: 857
<212> TYPE: DNA
<213> ORGANISM: Artificial sequence
<220> FEATURE:
<223> OTHER INFORMATION: stacked event

<400> SEQUENCE: 16
atgaaaatca tagtctaatc gtaaaaaatg tacagaagaa aagctagagc agaacaaaga 60
ttctatattc tggttccaat ttatcatcgc tttaacgtcc ctcagatttg atcgggcctt 120
aattaacccg ggcctgcagg tcgacggccg agtactggca ggatatatac cgttgtaatt 180
aagtgtttat gttgatattt taattatgtt tcatataaat ttgtcgtaat agtttaattg 240
ttaaatctaa ataaaagtat ttaaaaatag atattatatt ttttatgata tatataaata 300
tcatgaaact ttagaattta tggacaaaaa catcactatc cactagttaa tcatttctac 360
aaacgacatt tatttattta aaatggtcag aaaaattgtg acctaccagg aatgaggatt 420
tgattggagg gatgtaaacc aagttgatat ttttttctca cttgtgaaaa agatagtgtt 480
tggctggaat tttatgtatg ataaatttga tagggacttg cacttgagat tattttctgg 540
gttcttcatg cttttataat aacttgacta tcaaattctc tctttggatt ctacgacgtt 600
catatctatt tgtatggtgg cttcgagtag gaattttttt aaaagtattt gtgtttgata 660
tttacatatg tttttataca atgtttagaa ctacttatag tccatttcat cccttaagta 720
ggtacgcctt cctacattga caacaatatc gatactaatc gaactaaaac tcaatcaacg 780
cccatattcg acacttcaat ttggataata agtagagtat tttatagata tttgatttat 840
atgtaaatga ttttttt 857

<210> SEQ ID NO 17
<211> LENGTH: 806
<212> TYPE: DNA
<213> ORGANISM: Artificial sequence
<220> FEATURE:

<223> OTHER INFORMATION: targeted insertion event 91-74a

<400> SEQUENCE: 17

```
atgaaaatca tagtctaatc gtaaaaaatg tacagaagaa aagctagagc agaacaaaga     60
ttctatattc tggttccaat ttatcatcgc tttaacgtcc ctcagatttg atcgggcctt    120
aattaacccg ggcctgcagg tcgacggccg agttatgttt catataaatt tgtcgtaata    180
gtttaattgt taaatctaaa taaaagtatt taaaaataga tattatattt tttatgatat    240
atataaatat catgaaactt tagaatttat ggacaaaaac atcactatcc actagttaat    300
catttctaca aacgacattt atttatttaa aatggtcaga aaaattgtga cctaccagga    360
atgaggattt gattggaggg atgtaaacca agttgatatt tttttctcac ttgtgaaaaa    420
gatagtgttt ggctggaatt ttatgtatga taaatttgat agggacttgc acttgagatt    480
attttctggg ttcttcatgc ttttataata acttgactat caaattctct ctttggattc    540
tacgacgttc atatctattt gtatggtggc ttcgagtagg aattttttta aaagtatttg    600
tgtttgatat ttacatatgt ttttatacaa tgtttagaac tacttatagt ccatttcatc    660
ccttaagtag gtacgccttc ctacattgac aacaatatcg atactaatcg aactaaaact    720
caatcaacgc ccatattcga cacttcaatt tggataataa gtagagtatt ttatagatat    780
ttgatttata tgtaaatgat tttttt                                         806
```

<210> SEQ ID NO 18
<211> LENGTH: 277
<212> TYPE: DNA
<213> ORGANISM: Artificial sequence
<220> FEATURE:
<223> OTHER INFORMATION: targeted insertion event 91-74b

<400> SEQUENCE: 18

```
atgaaaatca tagtctaatc gtaaaaaatg tacagaagaa aagctagagc agaacaaaga     60
ttctatattc tggttccaat ttatcatcgc tttaacgtcc ctcagatttg atcgggcctt    120
aattaacccg ggcctgcagg tcgacggccg agtactggat aataggactg gatatttaca    180
tatttaaaac tcaatcaacg cccatattcg acacttcaat ttggataata agtagagtat    240
tttatagata tttgatttat atgtaaatga ttttttt                             277
```

<210> SEQ ID NO 19
<211> LENGTH: 900
<212> TYPE: DNA
<213> ORGANISM: Artificial sequence
<220> FEATURE:
<223> OTHER INFORMATION: targeted insertion event 92-13

<400> SEQUENCE: 19

```
atgaaaatca tagtctaatc gtaaaaaatg tacagaagaa aagctagagc agaacaaaga     60
ttctatattc tggttccaat ttatcatcgc tttaacgtcc ctcagatttg atcgggaaac    120
ataacttcgt atagcataca ttatacgaag ttatcaaaac gtcgtgagac agtttggttg    180
tagcgatcgc catggagcca tttacaaact gtctcaagtt atcaagtgtt tatgttgata    240
ttttaattat gtttcatata aatttgtcgt aatagtttaa ttgttaaatc taaataaaag    300
tatttaaaaa tagatattat atttttatg atatatataa atatcatgaa actttagaat    360
ttatggacaa aaacatcact atccactagt taatcatttc tacaaacgac atttatttat    420
ttaaaatggt cagaaaaatt gtgacctacc aggaatgagg atttgattgg agggatgtaa    480
accaagttga tatttttttc tcacttgtga aaaagatagt gtttggctgg aattttatgt    540
```

-continued

```
atgataaatt tgatagggac ttgcacttga gattattttc tgggttcttc atgcttttat    600

aataacttga ctatcaaatt ctctctttgg attctacgac gttcatatct atttgtatgg    660

tggcttcgag taggaatttt tttaaaagta tttgtgtttg atatttacat atgtttttat    720

acaatgttta gaactactta tagtccattt catcccttaa gtaggtacgc cttcctacat    780

tgacaacaat atcgatacta atcgaactaa aactcaatca acgcccatat tcgacacttc    840

aatttggata ataagtagag tattttatag atatttgatt tatatgtaaa tgattttttt    900
```